(12) United States Patent
Dow et al.

(10) Patent No.: US 7,741,300 B2
(45) Date of Patent: *Jun. 22, 2010

(54) METHODS OF USING NUCLEIC ACID VECTOR-LIPID COMPLEXES

(75) Inventors: Steven W. Dow, Littleton, CO (US); Robyn E. Elmslie, Littleton, CO (US); Jurgen Karl Johannes Schwarze, Witten (DE); Erwin W. Gelfand, Englewood, CO (US)

(73) Assignee: National Jewish Medical and Research Center, Denver, CO (US)

(*) Notice: Subject to any disclaimer, the term of this patent is extended or adjusted under 35 U.S.C. 154(b) by 847 days.

This patent is subject to a terminal disclaimer.

(21) Appl. No.: 11/320,019

(22) Filed: Dec. 27, 2005

(65) Prior Publication Data

US 2006/0223769 A1    Oct. 5, 2006

Related U.S. Application Data

(63) Continuation of application No. 10/012,597, filed on Nov. 30, 2001, now abandoned, which is a continuation-in-part of application No. 09/104,759, filed on Jun. 25, 1998, now Pat. No. 6,693,086.

(51) Int. Cl.
*A61K 48/00* (2006.01)
*C12N 15/88* (2006.01)
*C12N 15/63* (2006.01)

(52) U.S. Cl. .............. 514/44 R; 435/458; 435/320.1

(58) Field of Classification Search .......... 514/44; 435/458, 320.1
See application file for complete search history.

(56) References Cited

U.S. PATENT DOCUMENTS

| | | |
|---|---|---|
| 3,906,092 A | 9/1975 | Hilleman et al. |
| 4,452,775 A | 6/1984 | Kent |
| 4,956,296 A | 9/1990 | Fahnestock |
| 4,957,735 A | 9/1990 | Huang |
| 4,981,684 A | 1/1991 | MacKenzie et al. |
| 5,013,556 A | 5/1991 | Woodle et al. |
| 5,023,243 A | 6/1991 | Tullis |
| 5,043,164 A | 8/1991 | Huang et al. |
| 5,075,109 A | 12/1991 | Tice et al. |
| 5,087,617 A | 2/1992 | Smith |
| 5,178,860 A | 1/1993 | MacKenzie et al. |
| 5,234,811 A | 8/1993 | Beutler et al. |
| 5,248,670 A | 9/1993 | Draper et al. |
| 5,399,346 A | 3/1995 | Anderson et al. |
| 5,457,189 A | 10/1995 | Crooke et al. |
| 5,514,577 A | 5/1996 | Draper et al. |
| 5,543,152 A | 8/1996 | Webb et al. |
| 5,567,604 A | 10/1996 | Rando et al. |
| 5,576,302 A | 11/1996 | Cook et al. |
| 5,580,859 A | 12/1996 | Felgner et al. |
| 5,585,479 A | 12/1996 | Hoke et al. |
| 5,589,466 A | 12/1996 | Felgner et al. |
| 5,593,972 A | 1/1997 | Weiner et al. |
| 5,594,122 A | 1/1997 | Friesen |
| 5,595,756 A | 1/1997 | Bally et al. |
| 5,641,662 A | 6/1997 | Debs et al. |
| 5,643,578 A | 7/1997 | Robinson et al. |
| 5,658,891 A | 8/1997 | Draper et al. |
| 5,663,153 A | 9/1997 | Hutcherson et al. |
| 5,665,580 A | 9/1997 | Crooke et al. |
| 5,676,954 A | 10/1997 | Brigham |
| 5,679,354 A | 10/1997 | Morein et al. |
| 5,679,647 A | 10/1997 | Carson et al. |
| 5,681,944 A | 10/1997 | Crooke et al. |
| 5,686,101 A | 11/1997 | Tagawa et al. |
| 5,693,622 A | 12/1997 | Wolff et al. |
| 5,703,055 A | 12/1997 | Felgner et al. |
| 5,703,057 A | 12/1997 | Johnston et al. |
| 5,705,187 A | 1/1998 | Unger |
| 5,705,385 A | 1/1998 | Bally et al. |
| 5,723,335 A | 3/1998 | Hutcherson et al. |
| 5,736,152 A | 4/1998 | Dunn |
| 5,753,613 A | 5/1998 | Ansell et al. |
| 5,756,097 A | 5/1998 | Landucci et al. |
| 5,766,920 A | 6/1998 | Babbitt et al. |

(Continued)

FOREIGN PATENT DOCUMENTS

EP    0819758 A2    1/1998

(Continued)

OTHER PUBLICATIONS

Cornelie, S., et al. "Methylated cpG-Containing Plasmid Activates the Immune System", *Scandinavian Journal of Immunology* (2004) 59:143-151.

(Continued)

*Primary Examiner*—Anne Marie S Wehbe
(74) *Attorney, Agent, or Firm*—Sughrue Mion, PLLC

(57) ABSTRACT

This invention relates to a vaccine and a method for immune activation which is effective for eliciting both a systemic, non-antigen specific immune response and a strong antigen-specific immune response in a mammal. The method is particularly effective for protecting a mammal from a disease including cancer, a disease associated with allergic inflammation, an infectious disease, or a condition associated with a deleterious activity of a self-antigen. Also disclosed are therapeutic compositions useful in such a method.

9 Claims, 19 Drawing Sheets

U.S. PATENT DOCUMENTS

| | | | |
|---|---|---|---|
| 5,780,448 A | 7/1998 | Davis |
| 5,785,992 A | 7/1998 | Ansell et al. |
| 5,786,189 A | 7/1998 | Locht et al. |
| 5,804,566 A | 9/1998 | Carson et al. |
| 5,814,335 A | 9/1998 | Webb et al. |
| 5,817,856 A | 10/1998 | Tirosh et al. |
| 5,820,873 A | 10/1998 | Choi et al. |
| 5,827,703 A | 10/1998 | Debs et al. |
| 5,830,878 A | 11/1998 | Gorman et al. |
| 5,837,243 A | 11/1998 | Deo et al. |
| 5,843,770 A | 12/1998 | Ill et al. |
| 5,849,719 A | 12/1998 | Carson et al. |
| 5,854,418 A | 12/1998 | Chang et al. |
| 5,858,987 A | 1/1999 | Beer-Romero et al. |
| 5,877,309 A | 3/1999 | McKay et al. |
| 5,935,568 A | 8/1999 | Dow et al. |
| 5,955,059 A | 9/1999 | Gilchrest et al. |
| 5,965,542 A | 10/1999 | Wasan et al. |
| 5,968,909 A | 10/1999 | Agrawal et al. |
| 5,976,567 A | 11/1999 | Wheeler et al. |
| 5,981,501 A | 11/1999 | Wheeler et al. |
| 5,985,662 A | 11/1999 | Anderson et al. |
| 5,997,858 A | 12/1999 | Tovey et al. |
| 6,027,726 A | 2/2000 | Ansell |
| 6,027,732 A | 2/2000 | Morein et al. |
| 6,030,954 A | 2/2000 | Wu et al. |
| 6,030,955 A | 2/2000 | Stein et al. |
| 6,090,791 A | 7/2000 | Sato et al. |
| 6,107,062 A | 8/2000 | Hu et al. |
| 6,110,745 A | 8/2000 | Zhang et al. |
| 6,114,167 A | 9/2000 | Symonds et al. |
| 6,121,247 A * | 9/2000 | Huang et al. ............... 514/44 |
| 6,121,434 A | 9/2000 | Peyman et al. |
| 6,184,369 B1 | 2/2001 | Rando et al. |
| 6,194,388 B1 | 2/2001 | Krieg et al. |
| 6,207,646 B1 | 3/2001 | Krieg et al. |
| 6,207,819 B1 | 3/2001 | Manoharan et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,224,901 B1 | 5/2001 | Li et al. |
| 6,239,116 B1 | 5/2001 | Krieg et al. |
| 6,287,591 B1 | 9/2001 | Semple et al. |
| 6,316,024 B1 | 11/2001 | Allen et al. |
| 6,339,068 B1 | 1/2002 | Krieg et al. |
| 6,348,312 B1 | 2/2002 | Peyman et al. |
| 6,399,630 B1 | 6/2002 | Macfarlane |
| 6,406,705 B1 | 6/2002 | Davis et al. |
| 6,426,334 B1 | 7/2002 | Agrawal et al. |
| 6,429,199 B1 | 8/2002 | Krieg et al. |
| 6,475,784 B1 * | 11/2002 | Papkoff ............... 435/325 |
| 6,476,000 B1 | 11/2002 | Agrawal |
| 6,479,504 B1 | 11/2002 | Macfarlane et al. |
| 6,521,637 B2 | 2/2003 | Macfarlane |
| 6,534,484 B1 | 3/2003 | Wheeler et al. |
| 6,544,518 B1 | 4/2003 | Friede et al. |
| 6,558,670 B1 | 5/2003 | Friede et al. |
| 6,589,940 B1 | 7/2003 | Raz et al. |
| 6,605,708 B1 | 8/2003 | Habus et al. |
| 6,610,308 B1 | 8/2003 | Haensler |
| 6,610,661 B1 | 8/2003 | Carson et al. |
| 6,620,805 B1 | 9/2003 | Takle et al. |
| 6,627,615 B1 | 9/2003 | Debs et al. |
| 6,630,455 B1 | 10/2003 | Mitchell |
| 6,653,292 B1 | 11/2003 | Krieg et al. |
| 6,670,186 B1 | 12/2003 | Nair et al. |
| 6,693,086 B1 * | 2/2004 | Dow et al. ............... 514/44 |
| 6,727,230 B1 | 4/2004 | Hutcherson et al. |
| 6,815,429 B2 | 11/2004 | Agrawal |
| 6,821,957 B2 | 11/2004 | Krieg et al. |
| 6,835,395 B1 | 12/2004 | Semple et al. |
| 6,849,725 B2 | 2/2005 | Junghans et al. |
| 6,943,240 B2 | 9/2005 | Bauer et al. |
| 6,949,520 B1 | 9/2005 | Hartmann et al. |
| 7,001,890 B1 | 2/2006 | Wagner et al. |
| 7,105,495 B2 | 9/2006 | Agrawal et al. |
| 7,192,222 B2 | 10/2006 | Van Nest et al. |
| 2001/0036462 A1 | 11/2001 | Fong et al. |
| 2002/0009457 A1 | 1/2002 | Bowersock et al. |
| 2002/0055477 A1 | 5/2002 | Van Nest et al. |
| 2002/0065236 A1 | 5/2002 | Yew et al. |
| 2002/0091097 A1 | 7/2002 | Bratzler et al. |
| 2002/0110586 A1 | 8/2002 | Madden et al. |
| 2002/0119990 A1 | 8/2002 | Madden et al. |
| 2002/0137714 A1 | 9/2002 | Kandamilla et al. |
| 2002/0164341 A1 | 11/2002 | Davis et al. |
| 2002/0192184 A1 | 12/2002 | Carpentier et al. |
| 2003/0022852 A1 | 1/2003 | Van Nest et al. |
| 2003/0022854 A1 | 1/2003 | Dow et al. |
| 2003/0026801 A1 | 2/2003 | Weiner et al. |
| 2003/0050261 A1 | 3/2003 | Krieg et al. |
| 2003/0050268 A1 | 3/2003 | Krieg et al. |
| 2003/0059773 A1 | 3/2003 | Van Nest et al. |
| 2003/0082228 A1 | 5/2003 | Flowers et al. |
| 2003/0086900 A1 | 5/2003 | Low et al. |
| 2003/0091599 A1 | 5/2003 | Davis et al. |
| 2003/0100527 A1 | 5/2003 | Krieg et al. |
| 2003/0104044 A1 | 6/2003 | Semple et al. |
| 2003/0109469 A1 | 6/2003 | Carson et al. |
| 2003/0119774 A1 | 6/2003 | Foldvari et al. |
| 2003/0125279 A1 | 7/2003 | Junghans et al. |
| 2003/0129251 A1 | 7/2003 | Van Nest et al. |
| 2003/0139364 A1 | 7/2003 | Krieg et al. |
| 2003/0148316 A1 | 8/2003 | Lipford et al. |
| 2003/0148976 A1 | 8/2003 | Krieg et al. |
| 2003/0165478 A1 | 9/2003 | Sokoll et al. |
| 2003/0181406 A1 | 9/2003 | Schetter et al. |
| 2003/0186921 A1 | 10/2003 | Carson et al. |
| 2003/0191079 A1 | 10/2003 | Krieg et al. |
| 2003/0203861 A1 | 10/2003 | Carson et al. |
| 2003/0212026 A1 | 11/2003 | Krieg et al. |
| 2003/0224010 A1 | 12/2003 | Davis et al. |
| 2003/0232074 A1 | 12/2003 | Lipford et al. |
| 2003/0232780 A1 | 12/2003 | Carson et al. |
| 2003/0232856 A1 | 12/2003 | Macfarlane |
| 2004/0006010 A1 | 1/2004 | Carson et al. |
| 2004/0006034 A1 | 1/2004 | Raz et al. |
| 2004/0009949 A1 | 1/2004 | Krieg |
| 2004/0013688 A1 | 1/2004 | Wise et al. |
| 2004/0030118 A1 | 2/2004 | Wagner et al. |
| 2004/0038922 A1 | 2/2004 | Haensler et al. |
| 2004/0047869 A1 | 3/2004 | Garcon et al. |
| 2004/0053880 A1 | 3/2004 | Krieg et al. |
| 2004/0058883 A1 | 3/2004 | Phlips et al. |
| 2004/0067902 A9 | 4/2004 | Bratzler et al. |
| 2004/0067905 A1 | 4/2004 | Krieg et al. |
| 2004/0087534 A1 | 5/2004 | Krieg et al. |
| 2004/0087538 A1 | 5/2004 | Krieg et al. |
| 2004/0092468 A1 | 5/2004 | Schwartz et al. |
| 2004/0092472 A1 | 5/2004 | Krieg et al. |
| 2004/0097719 A1 | 5/2004 | Agrawal et al. |
| 2004/0106568 A1 | 6/2004 | Krieg et al. |
| 2004/0131628 A1 | 7/2004 | Bratzler et al. |
| 2004/0132677 A1 | 7/2004 | Fearon et al. |
| 2004/0132685 A1 | 7/2004 | Krieg et al. |
| 2004/0136948 A1 | 7/2004 | Fearon et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg et al. |
| 2004/0152656 A1 | 8/2004 | Krieg et al. |
| 2004/0152657 A1 | 8/2004 | Krieg et al. |
| 2004/0157791 A1 | 8/2004 | Dow et al. |
| 2004/0162258 A1 | 8/2004 | Krieg et al. |

| | | |
|---|---|---|
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0248837 A1 | 12/2004 | Raz et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0004144 A1 | 1/2005 | Carson et al. |
| 2005/0009774 A1 | 1/2005 | Krieg et al. |
| 2005/0013812 A1 | 1/2005 | Dow et al. |
| 2005/0031638 A1 | 2/2005 | Dalemans et al. |
| 2005/0032734 A1 | 2/2005 | Davis et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0064401 A1 | 3/2005 | Olek et al. |
| 2005/0070491 A1 | 3/2005 | Krieg et al. |
| 2005/0075302 A1 | 4/2005 | Hutcherson et al. |
| 2005/0079152 A1 | 4/2005 | Bot et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0130918 A1 | 6/2005 | Agrawal et al. |
| 2005/0148537 A1 | 7/2005 | Krieg et al. |
| 2005/0169888 A1 | 8/2005 | Hartman et al. |
| 2005/0171047 A1 | 8/2005 | Krieg et al. |
| 2005/0176672 A1 | 8/2005 | Scheule et al. |
| 2005/0181035 A1 | 8/2005 | Dow et al. |
| 2005/0181422 A1 | 8/2005 | Bauer et al. |
| 2005/0182017 A1 | 8/2005 | Krieg |
| 2005/0191342 A1 | 9/2005 | Tam et al. |
| 2005/0197314 A1 | 9/2005 | Krieg et al. |
| 2005/0209184 A1 | 9/2005 | Klinman et al. |
| 2005/0214355 A1 | 9/2005 | Klinman et al. |
| 2005/0215500 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0249794 A1 | 11/2005 | Semple et al. |
| 2005/0250726 A1 | 11/2005 | Krieg et al. |
| 2005/0256073 A1 | 11/2005 | Lipford et al. |
| 2005/0266015 A1 | 12/2005 | Clerici et al. |
| 2005/0267057 A1 | 12/2005 | Krieg |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0014713 A1 | 1/2006 | Agrawal et al. |
| 2006/0019909 A1 | 1/2006 | Agrawal et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |
| 2006/0074040 A1 | 4/2006 | Kandimalla et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0165773 A1 * | 7/2006 | Perez-Soler et al. .......... 424/450 |
| 2006/0172966 A1 | 8/2006 | Lipford et al. |
| 2006/0188913 A1 | 8/2006 | Krieg et al. |
| 2006/0189550 A1 | 8/2006 | Jiang et al. |
| 2006/0211639 A1 | 9/2006 | Bratzler et al. |
| 2006/0211641 A1 | 9/2006 | Agrawal et al. |
| 2006/0211644 A1 | 9/2006 | Krieg et al. |
| 2006/0223769 A1 | 10/2006 | Dow et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0251623 A1 | 11/2006 | Bachmann et al. |
| 2006/0251677 A1 | 11/2006 | Bachmann et al. |
| 2006/0286070 A1 | 12/2006 | Hartmann et al. |

FOREIGN PATENT DOCUMENTS

| | | |
|---|---|---|
| WO | WO93/25673 | 12/1993 |
| WO | WO94/04196 | 3/1994 |
| WO | WO99/66879 A2 | 12/1999 |

OTHER PUBLICATIONS

Sasaki, Shin, at al. "Adjuvant formulations and delivery systems for DNA vaccines", *Methods* (2003) 31:243-254.

C.J. Wheeler, et al. "A novel cationic lipid greatly enhances plasmid DNA delivery and expression in mouse lung", *Proc. Natl. Acad. Sci. USA* (1996) 93:11454-11459.

Liu, Y, et al. "Cationic Liposome-mediated intravenous Gene Delivery", *J. Biol. Chem.* (1995) 270(42):24864-24870.

Zou, Yiyu, et al. "Effective Treatment of Early Endobronchial Cancer With Regional Administration of Liposome-p53 Complexes", *J. Natl. Cancer Inst.* (1998) 90(15):1130-1137.

Oudrhiri, Noufissa, et al. "Gene transfer by guanidinium-cholesterol cationic lipids into airway epithelial cells in vitro and in vivo", *Proc. Natl. Acad. Sci. USA* (1997) 94:1651-1656.

Stribling, Roscoe, et al. "Aerosol gene delivery in vivo", *Proc. natl. Acad. Sci. USA* (1992) 89:11277-11281.

Nabel, Gary.J., et al. "Direct gene transfer with DNA-liposome complexes in melanoma: Expression, biologic activity, and lack of toxicity in humans", *Proc. Natl. Acad. Sci. USA* (1993) 90:11370-11311.

Li, Daqing, et al. "Combination Surgery and Nonviral Interleukin 2 Gene Therapy for Head and Neck Cancer", *Clinical Cancer Research* (1999) 5:1551-1556.

Philip, Ramila, et al. "In Vivo Gene Delivery", *J. Biol. Chem.* (1993) 268(22):16087-16090.

Hemmi, Hiroaki, et al. *Nature Immunology* (2002) 3(2):196-200.

Auf, Gregor, et al. "Implication of Macrophages in Tumor Rejection Induced by CpG-oligodeoxynucleotides Without Antigen", *Clinical Cancer Research* (2001) 7:3540-3543.

Vollmer, Jörg, et al. "Oligodeoxynucleotides lacking CpG dinucleotides mediate Toll-like receptor 9 dependent T helper type 2 biased immune stimulation", *Immunology* (2004) 113:212-223.

Raz, E., et al. "Cationic Lipids Inhibit Intradermal Genetic Vaccination", *Vaccines* (1994) 94:71-75.

Verma, Inder M., et al. "Gene Therapy—promises, problems and prospects", *Nature* (1997) 389:239-242.

Orkin, Stuart H., et al. "Report and Recommendation of the Panel to Assess the NIH Investment in Research on Gene Therapy", (1995) 1-41.

Gao, Xiang "Cationic Lipid-Based Gene Delivery: An Update", (undated) pp. 99-112.

Rodman, David M., et al. "Delivery of Genes Through the Lung Circulation", (undated) Chapter 9, pp. 181-191.

Freimark, Bruce D., et al. "Cationic Lipids Enhance Cytokine and Cell Influx Levels in the Lung Following Administration of Plasmid: Cationic Lipid Complexes", *J. Immunology* (1998) 160:4580-4586.

Yamamoto, Toshiko, et al. "Lipofection of Synthetic Oligodeoxyribonucleotide Having a Palindromic Sequence of AACGTT to Murine Splenocytes Enhances Interferon Production and Natural Killer Activity", *Microbiol. Immunol.* (1994) 38(10):831-836.

Ballas, Zuhair K., et al. "Induction of NK Activity in Murine and Human Cells by CpG Motifs in Oligodeoxynucleotides and Bacterial DNA", *Journal of Immunology* (1996) 157:1840-1845.

Krieg, Arthur M. "Lymphocyte activation by CpG dinucleotide motifs in prokaryotic DNA", *Trends in Microbiology* (1996) 4(2):73-77.

Pisetsky, David S. "The Immunologic Properties of DNA", *The Journal of Immunology* (1996) 156:421-423.

Sato, Yukio, et al. "Immunostimulatory DNA Sequences Necessary for Effective Intradermal Gene Immunization", *Science* (1996) 273:352-354.

Stacey, Katryn J., et al. "Macrophages Ingest and Are Activated by Bacterial DNA", *The Journal of Immunology* (1996) 157:2116-2122.

Sun, Siquan, et al. "Dual Function of Drosophila Cells as APCs for Native CD8$^+$ TCells: Implications for Tumor Immunotherapy", *Immunity* (1996) 4:555-564.

Liu, Yong, et al. "Factors influencing the efficiency of cationic liposome-mediated intravenous gene delivery", *Nature Biotechnology* (1997) 15:167-173.

Leitner, Wolfgang W., et al. "DNA and RNA-based vaccines: principles, progress and prospects" *Vaccine* (2000) 18:765-777.

Lesoon-Wood, Leslie A., et al. "Systemic Gene Therapy with p53 Reduces Growth and Metastases of a Malignant Human Breast Cancer in Nude Mice", *Human Gene Therapy* (1995) 6:395-405.

Okamoto, T., et al. *Proceedings of the American Association for Cancer Research* (1997) 38: Abstract #78.

Naitoh, J., et al. *Proceedings of the American Association for Cancer Research* (1998) 39: Abstract #2421.

Li, Xiu-Min, et al. "Mucosal IFN-λ Gene Transfer Inhibits Pulmonary Allergic Responses in Mice", *The Journal of Immunology* (1996) 157:3216-3219.

McLean, John W., et al. "Organ-specific endothelial cell uptake of cationic liposome-DNA complexes in mice", *American Journal of Physiology* (1997) 273:H3878-H404.

Pisetsky, David S. "Immune Activation by Bacterial DNA: A New Genetic Code", *Immunity* (1996) 5:303-310.

Roman, Mark, et al. "Immunostimulatory DNA sequences function as T helper—1—promoting adjuvants", *Nature Medicine* (1997) 3(8):849-854.

Rosenberg, Steven A., et al. "Regression of Established Pulmonary Metastases and Subcutaneous Tumor Mediated by the Systemic Administration of High-docse Recombinant Interleukin 2", *J. Exp. Med.* (1985) 161:1169-1188.

Scheule, Ronald K., et al. "Basis of Pulmonary Toxicity Associated with Cationic Lipid-Mediated Gene Transfer to the Mammalian Lung", *Human Gene Therapy* (1997) 8:689-707.

Templeton, Nancy S., et al. "Improved DNA: liposome complexes for increased systemic delivery and gene expression", *Nature Biotechnology* (1997) 15:647-652.

Gregoriadis, Gregory, et al. "Liposome-mediated DNA vaccination", *FEBS Letters* (1997) 402:107-110.

Ho, Rodney J.Y., et al. "Interactions of Target-sensitive Immunoliposomes with Herpes Simplex Virus", *Journal of Biological Chemistry* (1987) 262(29):13979-13984.

Ho, Rodney J.Y., et al. "Target-sensitive Immunoliposomes as an Efficient Drug Carrier for Antiviral Activity", *Journal of Biological Chemistry* (1987) 262(29):13973-13978.

Ho, Rodney J.Y., et al. "Target-sensitive Immunoliposomes: Preparation and Characterization", *Biochemistry* (1986) 25:5500-5506.

Allen, T.M., et al. "Large unilamellar liposomes with low uptake into the reticuloendothelial system", *FEBS Letters* (1987) 223(1):42-46.

Klibanov, Alexander L. "Amphipathic polyethyleneglycols effectively prolong the circulation time of liposomes", *FEBS Letters* (1990) 268(1):235-237.

Woodle, Martin C., et al. "Sterically stabilized liposomes", *Biochimica et Biophysica Acta* (1992) 1113:171-199.

Krieg, Arthur M., et al. "Oligodeoxynucleotide Modifications Determine the Magnitude of B Cell Stimulation by CpG Motifs", *Antisense & Nucl. Acid Drug Dev* (1996) 6:133-139.

Krieg, Arthur M., et al. "CpG motifs in bacterial DNA trigger direct B-cell activation", *Nature* (Lond.) (1995) 374:546-549.

Sparwasser, Tim, et al. "Bacterial DNA and immunostimulatory CpG oligonucleotides trigger maturation and activation of murine dendritic cells", *Eur. J. Immunol* (1998) 28:2045-2054.

Weiner, George J., et al. "Immunostimulatory oligodeoxynucleotides containing the CpG motif are effective as immune adjuvants in tumor antigen immunization", *PNAS* (USA) (1997) 94:10833-10837.

Zhao, Qiuyan, et al. "Comparison of Cellular Binding and Uptake of Antisense Phosphodiester, Phosphorothioate, and Mixed Phosphorothioate and Methylphosphonate Oligonucleotides", *Antisense Res and Dev* (1993) 3:53-66.

Whitmore, et al. "LPD lipopolyplex initiates a potent cytokine response and inhibits tumor growth", *Gene Ther.* (1999) 6:1867-1875.

Rudginsky, et al. "Antitumor activity of cationic lipid complexed with immunostimulatory DNA" *Mol Ther.* (2001) 4(4):347-355.

Norman, et al. "Liposome-mediated, nonviral gene transfer induces a systemic inflammatory response which can exacerbate pre-existing inflammation", *Gene Ther.* (2000) 7:1425-1430.

* cited by examiner

FIG. 6A
FIG. 6C
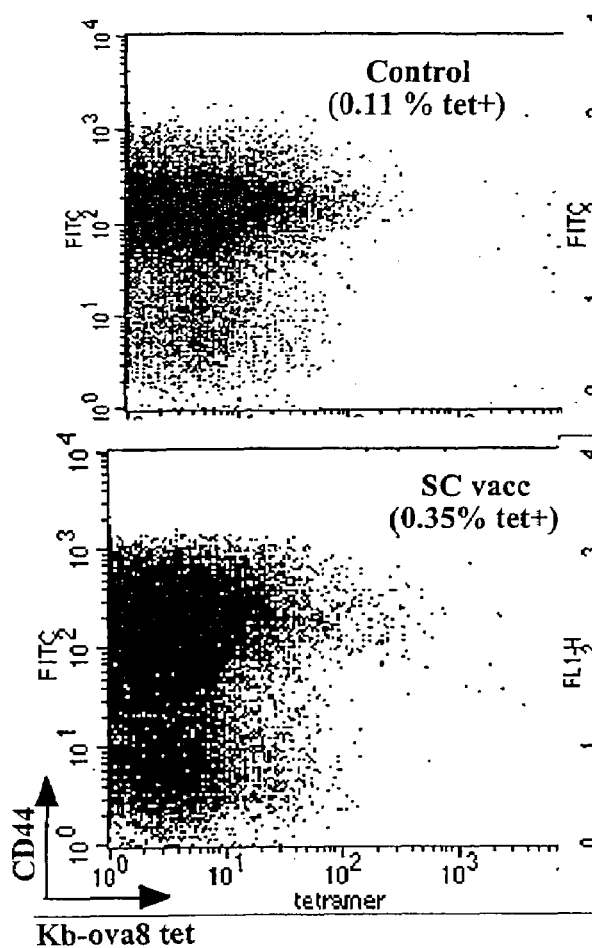
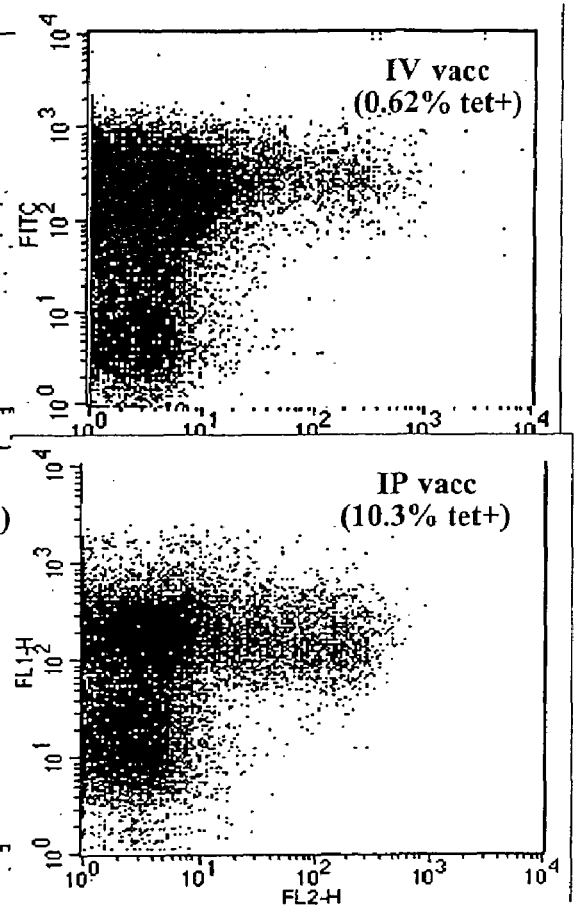
FIG. 6B
FIG. 6D

SEQUENCE LISTING

<160> NUMBER OF SEQ ID NOS: 1

<210> SEQ ID NO 1
<211> LENGTH: 8
<212> TYPE: PRT
<213> ORGANISM: Gallus gallus

<400> SEQUENCE: 1

Ser Ile Ile Asn Phe Glu Lys Leu
1               5

METHODS OF USING NUCLEIC ACID VECTOR-LIPID COMPLEXES

GOVERNMENT RIGHTS

This invention was supported in part by NIH Grant No. RO1 CA86224-01, awarded by the National Institutes of Health. The government has certain rights to this invention.

FIELD OF THE INVENTION

The present invention relates to a composition and method to elicit an immune response in a mammal. More particularly, the present invention includes vaccine to compositions and methods for eliciting systemic, antigen-specific immune responses, as well as systemic, non-antigen-specific immune responses, in a mammal.

BACKGROUND OF THE INVENTION

Three major types of disease in mammals which are amenable to elicitation and/or modulation of an immune response include infectious diseases, allergic inflammatory diseases and cancer. Infectious diseases are caused by infectious agents (i.e., infectious disease pathogens), examples of which include viruses, bacteria, parasites, prions, yeast and other fungi. In allergic inflammatory diseases, allergens cause the release of inflammatory mediators that recruit cells involved in inflammation in allergic or sensitized animals, the presence of which can lead to tissue damage and sometimes death. Cancer can result from an inherited inability to repair DNA, to prevent DNA damage or to prevent propagation of cells with damaged DNA, and/or from a biochemical dysfunction or genetic mutation which leads to uncontrolled cell proliferation and DNA synthesis.

Traditional reagents that are used in an attempt to protect a mammal from such diseases include reagents that destroy infectious agents or the cells involved in deregulated biological functions, or that modify the activity of such cells. Such reagents, however, can result in unwanted side effects. For example, anti-viral drugs that disrupt the replication of viral DNA also often disrupt DNA replication in normal cells in the treated patient. The use of anti-inflammatory and symptomatic relief reagents in allergic inflammation is a serious problem because of their side effects or their failure to attack the underlying cause of an inflammatory response. Other treatments with chemotherapeutic reagents to destroy cancer cells typically leads to side effects, such as bleeding, vomiting, diarrhea, ulcers, hair loss and increased susceptibility to secondary cancers and infections.

An alternative method of disease treatment includes modulating the immune system of a patient to assist the patient's natural defense mechanisms. Traditional reagents and methods used to attempt to regulate an immune response in a patient also result in unwanted side effects and have limited effectiveness. For example, immunopharmacological reagents used to treat cancer (e.g., interleukins) are short-lived in the circulation of a patient and are ineffective except in large doses. Due to the medical importance of immune regulation and to the inadequacies of existing immunopharmacological reagents, reagents and methods to regulate specific parts of the immune system have been the subject of study for many years. Vaccines can be used not only to prevent disease (prophylactic vaccines), but can also be used to treat established diseases (i.e., therapeutic vaccines). For example, a number of tumor antigens which are recognized by T lymphocytes of the immune system have been recently identified and are being considered as potential vaccine candidates.

Conventional vaccines generally include either (1) purified antigens, or (2) an attenuated form of a pathogen that can be administered to a patient to generate an immune response, but not cause serious disease or illness. Genetic vaccines contain a DNA sequence that encodes an antigen(s) against which the immune response is to be generated. For genetic vaccines to generate an antigen-specific immune response, the gene of interest must be expressed in the mammalian host. Gene expression has been accomplished by use of viral vectors (e.g., adenovirus, poxvirus) that express the foreign gene of interest in the vaccinated patient and induce an immune response against the encoded protein. Alternatively, plasmid DNA encoding a foreign gene has been used to induce an immune response. The primary routes of administration of these so-called "naked" DNA vaccines are intramuscular or percutaneous. It is generally accepted that viral vector systems induce better immune responses than naked DNA systems, probably because the viral delivery systems induce more inflammation and immune activation than naked DNA vaccines. The propensity of viral vaccines to induce non-specific immune responses, primarily as a result of viral component recognition by the complement cascade and by the elicitation of antigen-specific immune responses against specific components of the viral vector, also represents a potential drawback, however, since such immune responses often prevent readministration of the vaccine.

Therefore, there is need to provide better vaccines which can produce an immune response which is safe, antigen-specific, can be repeatedly administered, and which is effective to prevent and/or treat diseases amenable to treatment by elicitation of an immune response, such as infectious disease, allergy and cancer.

SUMMARY

One embodiment of the present invention relates to a vaccine. The vaccine includes the following components: (a) at least one immunogen for vaccinating a mammal; (b) a liposome; and (c) an isolated nucleic acid molecule that does not express the immunogen of (a). The immunogen and the isolated nucleic acid molecule are complexed to or within the liposome.

Preferably, the immunogen includes at least one epitope that elicits a cellular or humoral immune response in a mammal. In another embodiment, the immunogen is selected from the group consisting of a tumor antigen, an infectious disease pathogen antigen, an allergen and a self-antigen. The immunogen can include, but is not limited to, a peptide, a protein or portion thereof, a cell, a disrupted cell, a pathogenic microorganism, a carbohydrate, a lipid or any fractions or combinations thereof. In one embodiment, the vaccine comprises multiple immunogens.

In one embodiment, the isolated nucleic acid molecule is an oligonucleotide. In another embodiment, such an oligonucleotide contains a CpG motif that is immunogenic in a mammal. In yet another embodiment, such an oligonucleotide is demethylated. In another embodiment, the isolated nucleic acid molecule is a plasmid vector that does not contain a gene insert. Other nucleic acid molecules are also included in the invention, as set forth in the detailed description.

In one aspect, the isolated nucleic acid molecule encodes a cytokine, the nucleic acid sequence being operatively linked to a transcription control sequence. The cytokine can include, but is not limited to, hematopoietic growth factors, interleukins, interferons, immunoglobulin superfamily molecules, tumor necrosis factor family molecules and chemokines. In one embodiment, the cytokine is an interleukin. In another embodiment, the cytokine is selected from the group consisting of interleukin-2 (IL-2), interleukin-12 (IL-12), interleukin-18 (IL-18), and interleukin-15 (IL-15).

The liposome can be any suitable liposome, including, but not limited to, multilamellar vesicles, cationic liposomes, cholesterol complexed with the cationic lipids, and particularly, but not limited to, DOTMA and cholesterol; DOTAP and cholesterol; DOTIM and cholesterol; and DDAB and cholesterol. In one aspect, the composition has a nucleic acid to lipid ratio of from about 1:1 to about 1:64.

In one aspect, the vaccine includes a pharmaceutically acceptable excipient. Preferably the excipient includes, but is not limited to, 5-10% sucrose.

In one embodiment, the vaccine further comprises at least one cytokine (e.g., provided as a protein). Such a cytokine can include, but is not limited to, hematopoietic growth factors, interleukins, interferons, immunoglobulin superfamily molecules, tumor necrosis factor family molecules and chemokines. Preferred cytokines include, interleukin-2 (IL-2), interleukin-12 (IL-12), interleukin-18 (IL-18), and interleukin-15 (IL-15).

Yet another embodiment of the present invention relates to a method to elicit a systemic, immunogen-specific immune response in a mammal. The method includes the step of administering to the mammal a vaccine comprising: (a) at least one immunogen for vaccinating a mammal; (b) a liposome; and (c) an isolated nucleic acid molecule that does not express the immunogen of (a). The immunogen and the isolated nucleic acid molecule are complexed to or within the liposome. The step of administering can be by any route, including, but not limited to, intravenous, intraperitoneal, subcutaneous, intradermal, intranodal, intramuscular, transdermal, inhaled, intranasal, rectal, vaginal, urethral, topical, oral, intraocular, intraarticular, intracranial, and intraspinal. In one embodiment, the step of administering is by a combination of intravenous and intranodal administration. In another aspect, the step of administering is by a combination of intraperitoneal and intranodal administration. In yet another aspect, the step of administering is by a combination of intradermal and intranodal administration.

In one aspect, the immunogen is administered at a dose of from about 1 µg per individual mammal to about 1 mg per individual mammal. In another aspect, the immunogen is administered at a dose of from about 1 µg per individual mammal to about 100 µg per individual mammal. In yet another aspect, the immunogen is administered at a dose of from about 1 µg per individual mammal to about 10 µg per individual mammal. Preferably, administration of the vaccine to the mammal produces a result selected from the group consisting of immunization against the disease or condition and stimulation of effector cell immunity against the disease or condition.

BRIEF DESCRIPTION OF THE FIGURES

FIGS. 6A-6D are plots showing that immunization with LADC by: subcutaneous administration (FIG. 6B), intravenous administration (FIG. 6C), and intraperitoneal administration (FIG. 6D), elicits large numbers of antigen-specific CD8+ T cells (FIG. 6A is a control).

DETAILED DESCRIPTION OF THE INVENTION

Figure 1:
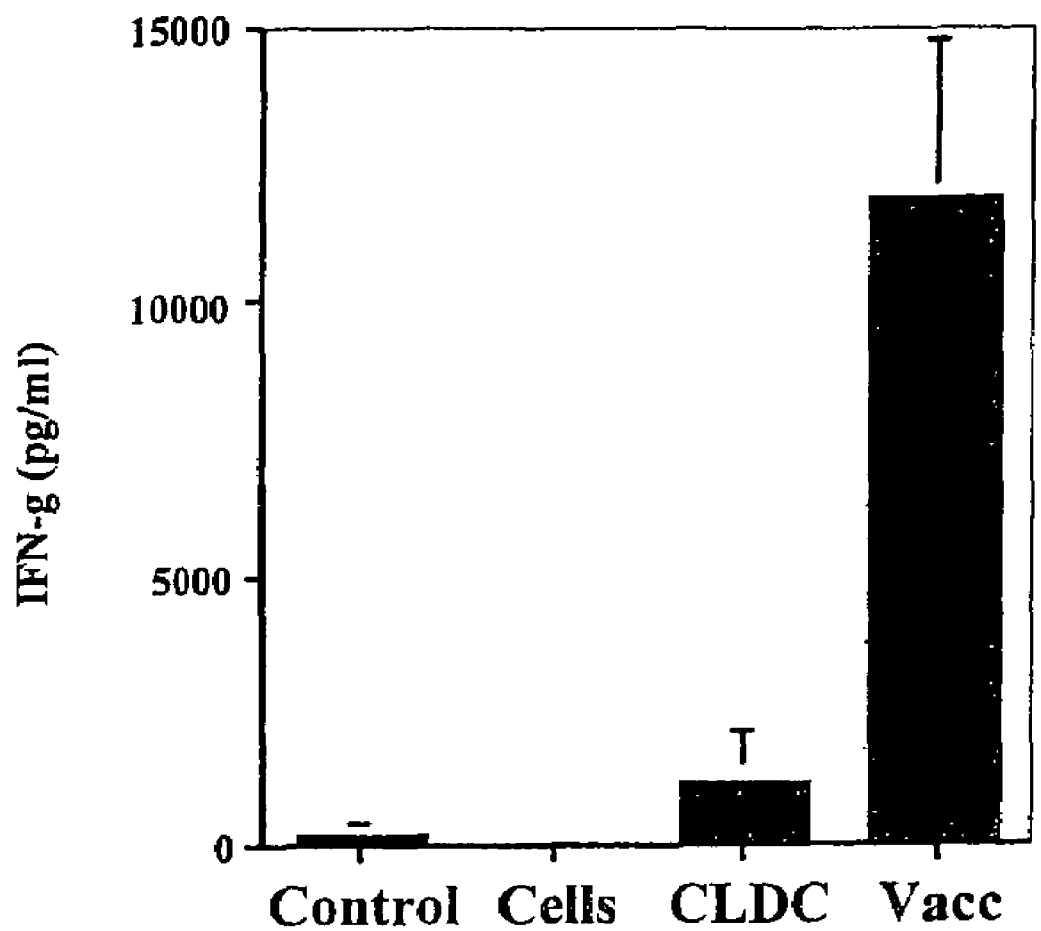
FIG. 1 is a bar graph showing that immunization with cationic lipid-DNA complexes combined with tumor lysates generates antitumor immunity.

The present invention generally relates to a novel immunization strategy and therapeutic compositions (e.g., vaccines) for eliciting an immune response in a mammal, and in particular, in a mammal that has a disease amenable to treatment by elicitation of an immune response. Diseases which are particularly amenable to treatment using the method of the present invention include any disease for which administration of a vaccine can provide protection against the disease, or reduce the symptoms of ongoing disease. For example, a vaccine of the present invention can be used to vaccinate against infectious disease, allergic inflammation and cancer.

More particularly, the immunization method of the present invention comprises the elicitation of an immune response in a mammal by administration of a therapeutic composition which includes: (a) at least one immunogen for vaccinating a mammal; (b) a liposome; and (c) an isolated nucleic acid molecule, as defined more particularly below, that does not encode the immunogen of (a). The immunogen and the isolated nucleic acid molecule are complexed to or within the liposome to form the vaccine.

The combination of nucleic acids and liposomes is highly immunostimulatory in vivo when administered by intravenous or intraperitoneal injection (See U.S. patent application Ser. No. 09/104,759, the entirety of which is incorporated herein by reference). The potency of this immune response was far greater than the response induced by administration of either nucleic acids or liposomes alone, and was particularly effective when administered by intravenous or intraperitoneal routes, although other routes could also generate an immune response. Moreover, this effect was independent of whether or not a protein was encoded by or expressed by the nucleic acids, and it was also independent of the source of the nucleic acids (e.g., mammalian, bacterial, insect, viral), the type of nucleic acids (e.g., DNA or RNA), and the type of lipids used. In addition, U.S. patent application Ser. No. 09/104,759 showed that the immune response generated by such a nucleic acid-lipid complex had potent anti-tumor, anti-allergy and anti-viral properties. As such, the nucleic acid-lipid complexes induced a strong, systemic, non-antigen-specific immune response, which resulted in the activation of multiple different immune effector cells in vivo. Immune activation induced by such nucleic acid/lipid complexes was quantitatively More potent than that induced by either LPS (endotoxin) or poly I/C (a classical inducer of antiviral immune responses). Furthermore, the type of immune stimulation induced (e.g., as characterized by the pattern of cytokines induced) also differed qualitatively from that induced by LPS or poly I/C. Finally, this effect did not appear to be associated with the complement cascade problems that have been experienced using viral delivery systems. In one embodiment of U.S. patent application Ser. No. 09/104,759, the combination of a liposome and a nucleic acid molecule that does not express a protein or peptide (non-coding or not linked to a suitable regulatory sequence) or have any other sequence-specific specificity. The non-coding nucleic acid molecule does not have sequence specific functionality, and includes empty vectors, non-coding oligonucleotides, and other nucleic acid sequences that do not encode a protein and do not have other sequence specificity.

The present invention relates to the combination of nucleic acid and liposomes as an effective adjuvant component of a vaccine for the delivery of an immunogen (e.g., protein, peptide, carbohydrate, lipid, whole cell immunogens or fractions thereof), and the use of such compositions for eliciting an immune response, as detailed below. More particularly, the present inventors demonstrate herein that the use of the combination of nucleic acids and lipids to deliver an immunogen (i.e., a protein, peptide, derivatives of proteins or peptides, carbohydrates, lipids, whole cells, whole cell lysates or disrupted cells, or organisms) to an animal provides a surprisingly effective means of generating an immune response against the immunogen. In particular, the present inventors have found that vaccination with lipid-DNA complexes combined with defined antigens can elicit strong antigen-specific CD8+ and CD4+ T cell responses in vivo, using even very low antigen doses, such that lipid-DNA vaccines of the present invention are sufficiently potent to elicit T cell responses against even weak antigens such as endogenous tumor antigens. These vaccines are more effective in eliciting T cell responses than currently available vaccine technologies, including dendritic cell immunization. In addition, the present inventors demonstrate herein that vaccination using lipid-DNA complexes and pools of tumor antigens prepared from tumor lysates is an effective means of generating CD8+ T cell responses against established tumors. Indeed, in general, the present inventors have found that the use of lipid-DNA complexes to vaccinate against protein antigens elicits surprisingly potent CD8+ T cell responses. This result is quite unexpected given the inherent difficulties associated with elicitation of CD8+ T cell responses against protein antigens in general. Immunization with lipid-DNA-antigen complexes according to the present invention also generates effective humoral immune responses. Importantly, the effectiveness of lipid-DNA-immunogen vaccines can be readily translated to large animal spontaneous disease models, including dogs and cats. Thus, the effectiveness of lipid-DNA-immunogen vaccines is not restricted to any one species of animal.

Due to the unexpected immunostimulatory properties of the nucleic acid:lipid complexes (i.e., the adjuvant portion of the vaccine), the immunization method of the present invention is particularly useful in human treatments because traditional adjuvants can be avoided. This is a particular advantage of the present method, since some traditional adjuvants can be toxic (e.g., Freund's adjuvant and other bacterial cell wall components) and others are relatively ineffective (e.g., aluminum-based salts and calcium-based salts). Moreover, the only adjuvants currently approved for use in humans in the United States are the aluminum salts, aluminum hydroxide and aluminum phosphate, neither of which stimulates cell-mediated immunity. In addition, traditional naked DNA delivery, which has been touted as having an adjuvant effect, is far less effective than the combination of nucleic acid and liposomes at stimulating a non-antigen-specific immune response. Finally, the present method can be used to repeatedly deliver the therapeutic composition described herein without consequences associated with some specific and non-specific arms of the immune response, and without the risks associated with some genetic vaccines, including those using viral vectors.

In further embodiments of the present invention, the present inventors have taken advantage of the non-antigen-specific immunostimulatory effect of the above-described method and have developed an even more powerful immunization strategy in which a nucleic acid sequence in the above nucleic acid-lipid complex encodes a cytokine that is expressed in the tissues of the mammal. Alternatively, the cytokine is provided in protein form with the immunogen. The combination of an antigen-specific immune response elicited by an immunogen, in conjunction with the powerful, non-antigen specific immune response elicited by the nucleic acid:lipid complex results in a vaccine that has great in vivo efficacy (See Examples section). This effect can be additionally enhanced by coadministration of a nucleic acid molecule encoding a cytokine such that the cytokine is expressed in the tissues or by coadministration of a protein cytokine together with the immunogen.

Moreover, the method of the present invention is particularly successful in mammals having cancer, because it induces a strong enough immune response to reduce or eliminate a primary tumor and to control any metastatic tumors that are already present, including large metastatic tumors. The method of the present invention is also particularly successful for vaccinating mammals against weak antigens or using very low antigen doses.

One embodiment of the present invention relates to a vaccine (used interchangeably with the phrase "therapeutic composition"). The vaccine comprises: (a) at least one immunogen for vaccinating a mammal; (b) a liposome; and (c) an isolated nucleic acid molecule that does not encode the immunogen of (a). The immunogen and the isolated nucleic acid molecule are complexed to or within the liposome.

Another embodiment of the present invention is a method to elicit a systemic, immunogen-specific immune response in a mammal. In this method, a vaccine of the present invention as described above is administered to a mammal. Administration of such a vaccine composition by the method of the present invention results in the elicitation of a systemic, immunogen-specific immune response in the mammal to which the vaccine is administered. As discussed above, this immune response has strong, systemic, anti-tumor, anti-allergic inflammation (i.e., protective), and anti-viral properties. Such properties include, but are not limited to, the elicitation of surprisingly potent $CD8^+$ T cell responses, $CD4^+$ T cell responses, and humoral immune responses.

Elicitation of an immune response in a mammal can be an effective treatment for a wide variety of medical disorders, and in particular, for cancer, allergic inflammation and/or infectious disease. As used herein, the term "elicit" can be used interchangeably with the terms "activate", "stimulate", "generate" or "upregulate". According to the present invention, "eliciting an immune response" in a mammal refers to specifically controlling or influencing the activity of the immune response, and can include activating an immune response, upregulating an immune response, enhancing an immune response and/or altering an immune response (such as by eliciting a type of immune response which in turn changes the prevalent type of immune response in a mammal from one which is harmful or ineffective to one which is beneficial or protective). For example, elicitation of a Th1-type response in a mammal that is undergoing a Th2-type response, or vice versa, may change the overall effect of the immune response from harmful to beneficial. Eliciting an immune response which alters the overall immune response in a mammal can be particularly effective in the treatment of allergic inflammation, mycobacterial infections, or parasitic infections. According to the present invention, a disease characterized by a Th2-type immune response (alternatively referred to as a Th2 immune response), can be characterized as a disease which is associated with the predominant activation of a subset of helper T lymphocytes known in the art as Th2-type T lymphocytes (or Th2 lymphocytes), as compared to the activation of Th1-type T lymphocytes (or Th1 lymphocytes). According to the present invention, Th2-type T lymphocytes can be characterized by their production of one or more cytokines, collectively known as Th2-type cytokines. As used herein, Th2-type cytokines include interleukin-4 (IL-4), interleukin-5 (IL-5), interleukin-6 (IL-6), interleukin-9 (IL-9), interleukin-10 (IL-10), interleukin-13 (IL-13) and interleukin-15 (IL-15). In contrast, Th1-type lymphocytes produce cytokines which include IL-2, TNFα and IFNγ. Alternatively, a Th2-type immune response can sometimes be characterized by the predominant production of antibody isotypes which include IgG1 (the approximate human equivalent of which is IgG4) and IgE, whereas a Th1-type immune response can sometimes be characterized by the production of an IgG2a or an IgG3 antibody isotype (the approximate human equivalent of which is IgG1, IgG2 or IgG3).

Preferably, the method of the present invention elicits an immune response against a tumor, an allergen or an infectious disease pathogen. In particular, eliciting an immune response in a mammal refers to regulating cell-mediated immunity. (i.e., helper T cell (Th) activity, cytotoxic T lymphocyte (CTL) activity, NK cell activity) and/or humoral immunity (i.e., B cell/immunoglobulin activity), including Th1-type and/or Th2-type cellular and/or humoral activity. In a preferred embodiment, the method of the present invention increases or elicits effector cell immunity against a tumor, an allergen or an infectious disease pathogen. As discussed above, the vaccine and method of the present invention are particularly effective at eliciting a $CD8^+$ T cell response. As used herein, effector cell immunity refers to increasing the number and/or the activity of effector cells in the mammal to which a composition is administered. In particular, T cell activity refers to increasing proliferation, cytokine production and/or cytoxicity of T cells in the area of the tumor cell or pathogen. Similarly, NK cell activity refers to increasing the proliferation, cytokine production and cytotoxic activity of NK cells. In the method of the present invention, effector cell immunity is elicited both systemically and in the area of the mammal in which the vaccine is primarily targeted, if any. According to the present invention, an effector cell includes a helper T cell, a cytotoxic T cell, a B lymphocyte, a macrophage, a monocyte and/or a natural killer cell. For example, the method of the present invention can be performed to increase the number of effector cells in a mammal that are capable of killing a target cell or releasing cytokines when presented with antigens derived from a tumor cell, an allergen or a pathogen. According to the present invention, elicitation of an immune response (i.e., a non-specific immune response) includes stimulation of non-specific immune cells, such as macrophages and neutrophils, as well as activation of effector cells such as NK cells and antigen-specific cells, including B lymphocytes and/or T lymphocytes, and induction of cytokine production.

Accordingly, the method of the present invention preferably elicits an immune response in a mammal such that the mammal is protected from a disease that is amenable to elicitation of an immune response, including cancer, allergic inflammation and/or an infectious disease. As used herein, the phrase "protected from a disease" refers to reducing the symptoms of the disease; reducing the occurrence of the disease, and/or reducing the severity of the disease. Protecting a mammal can refer to the ability of a therapeutic composition of the present invention, when administered to a mammal, to prevent a disease from occurring and/or to cure or to alleviate disease symptoms, signs or causes. As such, to protect a mammal from a disease includes both preventing disease occurrence (prophylactic treatment) and treating a mammal that has a disease or that is experiencing initial symptoms of a disease (therapeutic treatment). In particular, protecting a mammal from a disease is accomplished by eliciting an immune response in the mammal by inducing a beneficial or protective immune response which may, in some instances, additionally suppress (e.g., reduce, inhibit or block) an overactive or harmful immune response. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

More specifically, a vaccine as described herein, when administered to a mammal by the method of the present invention, preferably produces a result which can include alleviation of the disease (e.g., reduction of at least one symptom or clinical manifestation of the disease), elimination of the disease, reduction of a tumor or lesion associated with the disease, elimination of a tumor or lesion associated with the disease, prevention or alleviation of a secondary disease resulting from the occurrence of a primary disease (e.g., metastatic cancer resulting from a primary cancer), prevention of the disease, and stimulation of effector cell immunity against the disease.

One component of a vaccine or therapeutic composition of the present invention includes an immunogen for vaccinating an animal. According to the present invention, the terms "immunogen" and "antigen" can be used interchangeably, although the term "antigen" is primarily used herein to describe a protein, cellular composition (whole cell, cell lysate or disrupted cells) or organism (whole organism, lysate or disrupted cells) which elicits a humoral and/or cellular immune response (i.e., is antigenic), and the term "immunogen" is primarily used herein to describe a protein (including peptides and glycoproteins), cellular composition or organism, which elicits a humoral and/or cellular immune response in vivo, such that administration of the immunogen to a mammal mounts an immunogen-specific (antigen-specific) immune response against the same or similar proteins, cellular compositions or organisms that are encountered within the tissues of the mammal. Therefore, to vaccinate an animal means that an immune response is elicited against the immunogen as a result of administration of the immunogen. Vaccination preferably results in a protective or therapeutic effect, wherein subsequent exposure to the immunogen (or a source of the immunogen) elicits an immune response against the immunogen (or source) that reduces or prevents a disease or condition in the animal. The concept of vaccination is well known in the art. The immune response that is elicited by administration of a vaccine of the present invention can be any detectable increase in any facet of the immune response (e.g., cellular response, humoral response, cytokine production), as compared to in the absence of the administration of the vaccine. Preferably, an immunogen-specific immune response is detectable.

According to the present invention, the general use herein of the term "immunogen" refers to any portion of a protein (peptide, partial protein, full-length protein), wherein the protein is naturally occurring or synthetically derived, to carbohydrate antigens, to lipid antigens, to a whole cell, cellular lysate, or portion thereof, or to a microorganism, extract thereof, or other portion thereof, or to any combination of any of the above-mentioned immunogens, wherein the immunogen elicits a humoral and/or cellular immune response. An epitope is defined herein as a single antigenic site within a given immunogen that is sufficient to elicit an immune response. Those of skill in the art will recognize that T cell epitopes are different in size and composition from B cell epitopes, and that epitopes presented through the Class I MHC pathway differ from epitopes presented through the Class II MHC pathway. An immunogen can be as small as a single epitope, or larger, and can include multiple epitopes. As such, the size of an antigen or immunogen can be as small as about 5-12 amino acids (e.g., a peptide) and as large as: a full length protein, including a multimer and fusion proteins, chimeric proteins, whole cells, whole microorganisms, or portions thereof (e.g., lysates of whole cells or extracts of microorganisms). In preferred embodiments, the immunogen is selected from the group of a tumor antigen, an allergen or an antigen of an infectious disease pathogen (i.e., a pathogen antigen). According to the present invention, an immunogen suitable for use in the present composition or vaccine can include two or more epitopes from the same antigen, two or more epitopes or antigens from the same cell, tissue or organism, two or more different epitopes or antigens from different cells, tissues or organisms.

A tumor antigen that is useful as an immunogen or source of immunogen according to the present invention includes tumor antigens having epitopes that are recognized by T cells, tumor antigens having epitopes that are recognized by B cells, tumor antigens that are exclusively expressed by tumor cells, and tumor antigens that are expressed by tumor cells and by non-tumor cells. Tumor antigens can a tumor antigen including a protein or glycoprotein from a tumor cell, an epitope from a tumor antigen, an entire tumor cell, mixtures of tumor cells, and portions thereof (e.g., lysates). Immunogens useful in a composition according to the present invention can include any combination of epitopes, including from the same tumor antigen, from different tumor antigens, from different tumor cells, and from different individuals. Preferably, tumor immunogens useful in the present method have at least one T cell and/or B cell epitope. Therefore, delivery of the tumor immunogen to a tissue of a mammal elicits a tumor antigen-specific immune response against the tumor in the tissue of the mammal.

In one embodiment, tumor antigens useful in the present invention can be isolated or derived from an autologous tumor sample. An autologous tumor sample is derived from the mammal to whom the therapeutic composition is to be administered. Therefore, such antigens will be present in the cancer against which an immune response is to be elicited. In this embodiment, if all antigens from a given autologous source are administered together, it is not necessary to know which of the antigens in a given tumor sample is the most immunogenic (i.e., the best immunogens), since substantially all of the antigens expressed by the tumor sample can be administered to the mammal. In addition, eliciting an immune response against multiple tumor antigens/immunogens is likely to have the benefit of enhancing the therapeutic efficacy of the immune response against the cancer.

In another embodiment, the tumor antigen is isolated or derived from at least one, two or from a plurality of allogeneic tumor samples of the same histological tumor type. According to the present invention, a plurality of allogeneic tumor samples are tumor samples of the same histological tumor type, isolated from two or more mammals of the same species who differ genetically at least within the major histocompatibility complex (MHC), and typically at other genetic loci. Therefore, if administered together, the plurality of tumor antigens can be representative of the substantially all of the tumor antigens present in any of the individuals from which antigen is derived. This embodiment of the method of the present invention provides a vaccine which compensates for natural variations between individual patients in the expression of tumor antigens from tumors of the same histological tumor type. Therefore, administration of this therapeutic composition is effective to elicit an immune response against a variety of tumor antigens such that the same therapeutic composition can be administered to a variety of different individuals. In some embodiments, antigens from tumors of different histological tumor types can be administered to a mammal, in order to provide a very broad vaccine.

In a preferred embodiment, a tumor immunogen includes a tumor immunogen from a cancer selected from the group of melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias and metastatic cancers thereof.

According to the present invention, a pathogen immunogen that is useful in the present invention includes any immunogen from an infectious disease pathogen that can include pathogen immunogens having epitopes that are recognized by T cells, pathogen antigens having epitopes that are recognized by B cells, pathogen immunogens that are exclusively expressed by pathogens, and pathogen immunogens that are expressed by pathogens and by other cells. Pathogen immunogens can include whole cells and the entire pathogen organism, as well as lysates, extracts or other fractions thereof, including secreted toxins and/or spores produced by the pathogen. Preferably, pathogen immunogens useful in the present method have at least one T cell and/or B cell epitope and are exclusively expressed by pathogens (i.e., and not by the endogenous tissues of the infected mammal). Therefore, delivery of the pathogen immunogen to a tissue of a mammal elicits an antigen-specific immune response against the pathogen in the tissues of the mammal as well as systemically. In some instances, an immunogen can include organisms which may not be ordinarily considered to be pathogenic in a mammal, but against which immunization is nonetheless desired.

In one embodiment, the immunogen(s) can include at least two or preferably, a plurality of pathogen antigens that is representative of the substantially all of the antigens present in the infectious disease pathogen against which the vaccine is to be administered. In this embodiment, it is not necessary to know which of the antigens in a given pathogen is the most immunogenic (i.e., the best immunogens), since substantially all of the antigens expressed by the pathogen are administered to the mammal. In addition, eliciting an immune response against multiple pathogen antigens/immunogen is likely to have the benefit of enhancing the therapeutic efficacy of the immune response against the infectious disease. In other embodiments, immunogens from two or more different strains of the same pathogen or from different pathogens can be administered to increase the therapeutic efficacy and/or efficiency of the vaccine.

According to the present invention, a pathogen immunogen includes, but is not limited to, an immunogen that is expressed by a bacterium, a virus, a parasite, a prion or a fungus. Preferred pathogen immunogens for use in the method of the present invention include immunogens which cause a chronic or an acute infectious disease in a mammal. For example, some preferred pathogen immunogens for use in the present method are immunogens from pathogens that cause chronic infections, including, but not limited to, immunodeficiency virus (HIV), *Mycobacterium tuberculosis*, herpesvirus, papillomavirus, *Leishmania, Toxoplasma, Cryptococcus, Blastomyces, Histoplasma*, and *Candida*. Also. included would be antibiotic resistant strains of bacteria that can cause chronic infections, such as *Staphylococcus, Pseudomonas, Streptococcus, Enterococcus*, and *Salmonella*. Additionally, for immunization against acute disease, preferred pathogens from which immunogens can be derived include, but are not limited to, *Bacillus anthracis, Francisella, Yersenia, Pasteurella*, small pox, and other gram negative and gram positive bacterial pathogens.

In another embodiment of the present invention, a pathogen immunogen for use in the method or composition of the present invention includes an immunogen from a virus. As discussed above, the present inventors have found that the composition and method of the present invention are particularly useful in the treatment of and protection against viral infections. Specifically, the nucleic acid:lipid complex administered by the method of the present invention elicits a strong, systemic, non-antigen-specific, anti-viral response in vivo, and the viral antigen further elicits a strong, viral immunogen-specific immune response in addition to the above-described systemic immune response. In a preferred embodiment, the immunogen is from a virus selected from the group of human immunodeficiency virus, Epstein Barr virus, other Herpes viruses, papilloma virus, and Hepatitis viruses.

According to the present invention, an allergen immunogen includes a full-length allergen, a portion of the allergen or a homologue of the allergen protein, and includes allergens having epitopes that are recognized by T cells, allergens having epitopes that are recognized by B cells, and any allergens that are a sensitizing agent in diseases associated with allergic inflammation. Preferred allergens to use in the therapeutic composition of the present invention include plant pollens, drugs, foods, venoms, insect excretions, molds, animal fluids, animal hair and animal dander. Sensitization to an allergen refers to being previously exposed one or more times to an allergen such that an immune response is developed against the allergen. Responses associated with an allergic reaction (e.g., histamine release, rhinitis, edema, vasodilation, bronchial constriction, airway inflammation), typically do not occur when a naive individual is exposed to the allergen for the first time, but once a cellular and humoral immune response is produced against the allergen, the individual is "sensitized" to the allergen. Allergic reactions then occur when the sensitized individual is re-exposed to the same allergen (e.g., an allergen challenge). Once an individual is sensitized to an allergen, the allergic reactions can become worse with each subsequent exposure to the allergen, because each re-exposure not only produces allergic symptoms, but further increases the level of antibody produced against the allergen and the level of T cell response against the allergen.

In one embodiment, the immunogen(s) useful in the present composition can be isolated or derived from multiple allergens. In this embodiment of the present invention, the plurality allergens and/or allergen epitopes is representative of the substantially all of the epitopes present in one allergen or from a class of allergens, for example.

In another embodiment of the present invention, an immunogen for use in the method or composition of the present invention includes a normal, self-antigen, wherein immunization against such an antigen induces a therapeutic outcome. The present inventors have found that the vaccination composition and method of the present invention is effective to break self tolerance, and therefore, when elicitation of an immune response against a self-antigen (one to which the mammal's immune system is normally tolerant) would be therapeutic, the immunogen can be a self-antigen. Such self-antigens include, but are not limited to, growth factors, signaling molecules, and normal cells. For example, in conditions where abnormal blood vessel growth is experienced, the present invention can be used to immunize the patient against an angiogenic growth factor or receptor thereof, such as the VEGF receptor. As another example, immunization against a signaling molecule is used to treat a neurologic disease. Such immunogens include proteins, portions thereof, carbohydrates, lipid molecules, normal cells, and fractions thereof. A normal cell useful as an immunogen includes, but is not limited to, an endothelial cell (or a fraction thereof). Such a cell may be particularly useful in an immunization strategy against cancer.

Other immunogens useful in the present invention and combinations of immunogens will be apparent to those of skill in the art. The present invention is not restricted to the use of the immunogens as described above.

One component of the vaccine of the present invention is a nucleic acid molecule that does not encode the immunogen used in the vaccine. This does not preclude the possibility that the nucleic acid molecule encodes a protein or peptide that is not the immunizing antigen (immunogen), although it may be, in some aspects, preferable that the nucleic acid molecule does not encode any protein or peptide that would be substantially immunogenic (e.g., sufficient to elicit a substantial immune response), or alternatively that the nucleic acid molecule does not encode a protein, or that the nucleic acid molecule has no sequence specific functionality (discussed below). In one embodiment, the nucleic acid molecule encodes a protein, which could even include the immunizing antigen, but the molecule is not operatively linked to a transcription control sequence so that as a result, no protein or peptide is expressed by the molecule. In another embodiment, the vaccine can include a nucleic acid molecule that encodes an immunogen in addition to the immunogen described above, or in place of the immunogen described above.

According to the present invention, an isolated nucleic acid molecule or nucleic acid sequence, is a nucleic acid molecule or sequence that has been removed from its natural milieu. As such, "isolated" does not necessarily reflect the extent to which the nucleic acid molecule has been purified. An isolated nucleic acid molecule useful in the present composition can include DNA, RNA, or any derivatives of either DNA or RNA. An isolated nucleic acid molecule can be double stranded (i.e., containing both a coding strand and a complementary strand) or single stranded. An isolated nucleic, acid molecule useful in the present composition can include oligonucleotides and larger sequences, including both nucleic acid molecules that encode a protein or a fragment thereof (in one aspect, such protein is not the immunogen to be used with the given nucleic acid molecule in a vaccine according to the present invention), and nucleic acid molecules that comprise regulatory regions, introns, or other non-coding DNA or RNA. An isolated nucleic acid molecule can include a nucleic acid vector (e.g., a plasmid vector), which is preferably an "empty vector", described in more detail below, or any fragment of such a vector. An isolated nucleic acid molecule can include naturally occurring nucleic acid sequences, and sequences that are not from a naturally occurring sequence, such as a sequence of randomly generated nucleotides. In one embodiment, the nucleic acid molecule is not an antisense nucleic acid molecule (i.e., is not complementary to a sequence in a coding strand of DNA or to mRNA in the cells of a patient and/or does not specifically hybridize under stringent conditions to a coding strand of DNA or to mRNA in the cells of a patient), or is not a functional antisense molecule (e.g., does not have an ability to inhibit gene function even if it is a complementary sequence). In another embodiment, the nucleic acid molecule is not a viral nucleic acid, such as a viral vector or a nucleic acid encoding a viral protein(s). In another embodiment, the nucleic acid molecule is not a ribozyme.

Nucleic acid molecules useful in a therapeutic composition of the present invention can be eukaryotic or prokaryotic nucleic acids. Therefore, the nucleic acid molecule can be derived from any source, including mammalian, bacterial, insect, or viral sources, since the present inventors have discovered that the source of the nucleic acid does not have a significant effect on the ability to elicit an immune response when the nucleic acid is complexed with liposomes. In one embodiment of the present invention, the nucleic acid molecule used in a therapeutic composition of the present invention is not a bacterial nucleic acid molecule.

Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably. As used herein, a "coding" nucleic acid sequence refers to a nucleic acid sequence which encodes at least a portion of a peptide or protein (e.g. a portion of an open reading frame), and can more particularly refer to a nucleic acid sequence encoding a peptide or protein which, when operatively linked to a transcription control sequence, can express the peptide or protein. A "non-coding" nucleic acid sequence refers to a nucleic acid sequence which does not encode any portion of a peptide or protein. According to the present invention, "non-coding" nucleic acids can include regulatory regions of a transcription unit, such as a promoter region. According to the present invention, a nucleic acid molecule that "does not express" a peptide or protein can include both coding and non-coding nucleic acids, but in the case of the coding nucleic acids, the nucleic acid sequence is not provided in a form that can readily express the peptide or protein. For example, the sequence may not be operatively linked to an appropriate transcription control sequence so that the peptide or protein is not expressed when the nucleic acid molecule enters a cell. The term, "empty vector" is generally considered to be a type of "non-coding" nucleic acid molecule, and particularly refers to a nucleic acid sequence in the absence of a protein coding portion other than a selectable marker, such as a plasmid vector without a gene insert. Some empty vectors, and particularly those that are commercially available, may encode one or more selection markers, but such markers are not important to the inclusion of the nucleic acid molecule in the vaccine of the invention. Moreover, it is not believed that the selectable markers present in such empty vectors, even if expressed, would elicit a significant immune response, if any. Therefore, selectable markers encoded in vectors are not considered to be immunogens according to the present invention. Preferably, non-coding nucleic acids used in the present invention do not include antisense molecules, ribozymes, or other such nucleic acid molecules which may not encode a protein, but which have another function that is related to the sequence specificity of the molecule. Essentially, the nucleic acid molecule of the present invention preferably does not have any sequence specific functionality, in that the nucleic acids are used as a chemical composition in conjunction with a liposome, rather than for the purpose of encoding a particular protein, or executing a sequence-specific function associated with antisense or ribozymes.

A nucleic acid molecule that is a component of the vaccine or therapeutic composition of the present invention does not encode a superantigen. It is noted, however, that a protein superantigen may be added to the vaccine of the present invention, if desired to further enhance an immune response. A superantigen is defined herein as the art-recognized term. More particularly, a superantigen is a molecule within a family of proteins that binds to the extracellular portion of an MHC molecule (i.e., not in the peptide binding groove) to form and MHC:superantigen complex. The activity of a T cell can be modified when a TCR binds to an MHC:superantigen complex. Under certain circumstances, an MHC:superantigen complex can have a mitogenic role (i.e., the ability to stimulate the proliferation of T cells) or a suppressive role (i.e., deletion of T cell subsets).

A nucleic acid molecule can be isolated from a natural source, or it can be produced using recombinant DNA technology (e.g., polymerase chain reaction (PCR) amplification, cloning) or chemical synthesis. Nucleic acid molecules can be generated or modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof.

Typically, an oligonucleotide has a nucleic acid sequence from about 1 to about 500 nucleotides, and more typically, is at least about 5 nucleotides in length, or any length increasing by whole integers (e.g., 6, 7, 8, 9, 10 and so on), up to about 500 nucleotides. In a preferred embodiment, an oligonucleotide for use in the present invention includes an oligonucleotide containing a cytosine-guanine (CpG) motif that is immunogenic in a mammal. In another embodiment, the oligonucleotide is demethylated. Methylation of CpG motifs in DNA is involved in the control of gene expression and in several other epigenic effects. It suppresses the immunostimulation properties of bacterial or viral DNAs that contain CpGs. It is further known in the art that bacterial DNA and synthetic oligodeoxynucleotides containing unmethylated CpG-motifs in a particular sequence context can activate vertebrate immune cells.

A vaccine or therapeutic composition of the present invention also includes a liposome component. According to the present invention, a liposome comprises a lipid composition that is capable of fusing with the plasma membrane of a cell, thereby allowing the liposome to deliver a nucleic acid molecule and/or a protein composition into a cell. A liposome is also capable of either incorporating an immunogen on its surface or incorporating the immunogen internally. Suitable liposomes for use with the present invention include any liposome. In fact, the present inventors have demonstrated that the immune stimulatory effect of the combination of liposomes and nucleic acids is not limited to a particular type of liposome. Some preferred liposomes of the present invention include those liposomes commonly used in, for example, gene delivery methods known to those of skill in the art. Some preferred liposome delivery vehicles comprise multilamellar vesicle (MLV) lipids and extruded lipids, although the invention is not limited to such liposomes. Methods for preparation of MLV's are well known in the art and are described, for example, in U.S. patent application Ser. No. 09/104,759, ibid. According to the present invention, "extruded lipids" are lipids which are prepared similarly to MLV lipids, but which are subsequently extruded through filters of decreasing size, as described in Templeton et al., 1997, *Nature Biotech.*, 15:647-652, which is incorporated herein by reference in its entirety. Small unilamellar vesicle (SUV) lipids can also be used in the composition and method of the present invention and have been shown to be effective in combination with nucleic acids for eliciting an immune response (see U.S. patent application Ser. No. 09/104,759, ibid.). Other preferred liposome delivery vehicles comprise liposomes having a polycationic lipid composition (i.e., cationic liposomes). For example, cationic liposome compositions include, but are not limited to, any cationic liposome complexed with cholesterol, and without limitation, include DOTMA and cholesterol, DOTAP and cholesterol, DOTIM and cholesterol, and DDAB and cholesterol. Liposomes of the present invention can be any size, including from about 10 and 1000 nanometers (nm), or any size in between.

Complexing a liposome with a nucleic acid molecule can be achieved using methods standard in the art (see, for example, methods in U.S. patent application Ser. No. 09/104, 759, ibid.). According to the present invention a cationic lipid:DNA complex is also referred to herein as a CLDC, and a cationic lipid:RNA complex is also referred to herein as CLRC. A cationic lipid:DNA complex, wherein the DNA is an empty vector can be referred to as EV/CLDC. A CLDC that is further complexed with an immunogen according to the present invention can be referred to as a lipid-antigen-DNA complex (LADC) or as a vaccine (Vacc) or therapeutic composition.

A suitable concentration of a nucleic acid molecule to add to a liposome includes a concentration effective for delivering a sufficient amount of nucleic acid molecule into a mammal such that a systemic immune response is elicited. Preferably, from about 0.1 µg to about 10 µg of nucleic acid molecule of the present invention is combined with about 8 nmol liposomes, more preferably from about 0.5 µg to about 5 µg of nucleic acid molecule is combined with about 8 nmol liposomes, and even more preferably about 1.0 µg of nucleic acid molecule is combined with about 8 nmol liposomes. In one embodiment, the ratio of nucleic acids to lipids (µg nucleic acid:nmol lipids) in a composition of the present invention is preferably at least about 1:1 nucleic acid:lipid by weight (i.e., 1 µg nucleic acid: 1 nmol lipid), and more preferably, at least about 1:5, and more preferably at least about 1:10, and even more preferably at least about 1:20. Ratios expressed herein are based on the amount of cationic lipid in the composition, and not on the total amount of lipid in the composition. In another embodiment, the ratio of nucleic acids to lipids in a composition of the present invention is preferably from about 1:1 to about 1:64 nucleic acid:lipid by weight; and more preferably, from about 1:5 to about 1:50 nucleic acid:lipid by weight; and even more preferably, from about 1:10 to about 1:40 nucleic acid:lipid by weight; and even more preferably, from about 1:15 to about 1:30 nucleic acid:lipid by weight. Another particularly preferred ratio of nucleic acid:lipid is from about 1:8 to 1:16, with 1:8 to 1:32 being more preferred. Typically, while non-systemic routes of nucleic acid administration (e.g., intramuscular, intratracheal, intradermal) would use a ratio of about 1:1 to about 1:3, systemic routes of administration according to the present invention can use much less nucleic acid as compared to lipid and achieve equivalent or better results than non-systemic routes. Moreover, compositions designed for gene therapy/gene replacement, even when administered by intravenous administration, typically use more nucleic acid (e.g., from 6:1 to 1:10, with 1:10 being the least amount of DNA used) as compared to the systemic immune activation composition and method of the present invention.

Complexing an immunogen with a liposome and nucleic acid molecule is accomplished in a straightforward manner. The immunogen can be complexed with a preformed complex of nucleic acid and liposome, or it can be complexed with the liposome at the same time as the nucleic acid molecule. The immunogen can be effectively complexed with the liposome simply by gently mixing the immunogen and the liposome (and the nucleic acid) together, preferably in a suitable excipient (e.g., 5-10% sucrose or 5-10% lactose). The immunogen can also be incorporated into the liposome as the liposome is formulated (e.g., rehydrated). The immunogen can be mixed with the preformed lipid and nucleic acid complexes; mixed with the preformed lipid, followed by adding the nucleic acid; or can be mixed with the nucleic acid and then, together, added to preformed liposomes.

A suitable concentration of an immunogen to add to a liposome includes a concentration effective for delivering a sufficient amount of immunogen into a mammal such that an immunogen-specific immune response is elicited, at least at or near the site of administration, and preferably, systemically. Preferably, from about 1 µg immunogen per individual mammal to about 1 mg immunogen per individual mammal is combined with about 8 nmol liposomes (or other suitable amount of liposomes which can be determined by the skilled artisan), more preferably from about 1 µg immunogen per individual mammal to about 100 µg immunogen per individual mammal is combined with about 8 nmol liposomes, and even more preferably from about 1 µg immunogen per individual mammal to about 10 µg immunogen per individual mammal is combined with about 8 nmol liposomes. In one embodiment, at least about 0.1 µg immunogen per individual mammal, and more preferably at least about 1 µg immunogen per individual mammal, and more preferably, at least about 5 μg immunogen per individual mammal, and more preferably at least about 10 μg immunogen per individual mammal is added to a liposome composition of the present invention.

The vaccine of the present invention is capable of delivering the immunogen to a multitude of tissues, including spleen, lymph node, pulmonary tissues, and liver. The method of the present invention is not limited to delivery by intravenous or intraperitoneal routes, since the present inventors have found that other routes and combinations of routes are also quite effective at eliciting an immunogen-specific immune response. For example, the inventors have found that the combination of any of intravenous, intraperitoneal or intradermal administration with intranodal administration (into the lymph node) is particularly effective for eliciting an immune response.

A liposome delivery vehicle of the present invention can be modified to target a particular site in a mammal, thereby targeting and making use of a nucleic acid molecule of the present invention at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. In one embodiment, other targeting mechanisms, such as targeting by addition of exogenous targeting molecules to a liposome (i.e., antibodies) may not be a necessary component of the liposome of the present invention, since effective immune activation at immunologically active organs can already be provided by the composition when the route of delivery is intravenous or intraperitoneal, without the aid of additional targeting mechanisms. However, in some embodiments, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., 1986, *Biochemistry* 25: 5500-6; Ho et al., 1987a, *J Biol Chem* 262: 13979-84; Ho et al., 1987b, *J Biol Chem* 262: 13973-8; and U.S. Pat. No. 4,957,735 to Huang et al., each of which is incorporated herein by reference in its entirety). In one embodiment, if avoidance of the efficient uptake of injected liposomes by reticuloendothelial system cells due to opsonization of liposomes by plasma proteins or other factors is desired, hydrophilic lipids, such as gangliosides (Allen et al., 1987, *FEBS Lett* 223: 42-6) or polyethylene glycol (PEG)-derived lipids (klibanov et al., 1990, *FEBS Lett* 268: 235-7), can be incorporated into the bilayer of a conventional liposome to form the so-called sterically-stabilized or "stealth" liposomes (Woodle et al., 1992, *Biochim Biophys Acta* 1113: 171-99). Variations of such liposomes are described, for example, in U.S. Pat. No. 5,705,187 to Unger et al., U.S. Pat. No. 5,820,873 to Choi et al., U.S. Pat. No. 5,817,856 to Tirosh et al.; U.S. Pat. No. 5,686,101 to Tagawa et al.; U.S. Pat. No. 5,043,164 to Huang et al., and U.S. Pat. No. 5,013,556 to Woodle et al., all of which are incorporated herein by reference in their entireties).

A liposome delivery vehicle is preferably capable of remaining stable in a mammal for a sufficient amount of time to deliver a nucleic acid molecule and immunogen to a preferred site in the mammal. A liposome component of the vaccine or therapeutic composition of the present invention is preferably stable in the mammal into which it has been administered for at least about 30 minutes, more preferably for at least about 1 hour and even more preferably for at least about 24-72 hours.

In another embodiment of the present invention, a vaccine or therapeutic composition further comprises a pharmaceutically acceptable excipient. As used herein, a pharmaceutically acceptable excipient refers to any substance suitable for delivering a therapeutic composition useful in the method of the present invention to a suitable in vivo or ex vivo site. Preferred pharmaceutically acceptable excipients are capable of maintaining a nucleic acid molecule and/or immunogen in a form that, upon arrival of the nucleic acid molecule and/or immunogen to a cell, the nucleic acid molecule and/or protein are capable of contacting and/or entering the cell and eliciting an immune response at or near the site of the cell. Suitable excipients of the present invention include excipients or formularies that transport, but do not specifically target the vaccine to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Particularly preferred excipients include non-ionic diluents, with preferred non-ionic buffer being 5%-10% sucrose or 5-10% lactose in water.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Therapeutic compositions of the present invention can be sterilized by conventional methods and/or lyophilized.

In one embodiment of the invention, the vaccine or therapeutic composition can additionally include either a cytokine or a nucleic acid molecule that encodes a cytokine (also referred to herein as a "cytokine-encoding nucleic acid molecule"). The nucleic acid molecule encoding a cytokine is typically provided as a recombinant molecule. The phrase "recombinant molecule" or "recombinant nucleic acid molecule" primarily refers to a nucleic acid molecule or nucleic acid sequence operatively linked to a transcription control sequence, but can be used interchangeably with the phrase "nucleic acid molecule" which is administered to a mammal. The nucleic acid molecule can encode a full-length cytokine, at least a portion of a full-length cytokine that is biologically active (i.e., has substanstantially similar biological activity as the naturally occurring cytokine), or a homologue of the cytokine that is biologically active. As used herein, "at least a portion of a cytokine" refers to a portion of a cytokine protein having cytokine activity and being capable of binding to a cytokine receptor. Preferably, a cytokine-encoding nucleic acid molecule includes an entire coding region of a cytokine. As used herein, a homologue of a cytokine is a protein having an amino acid sequence that is sufficiently similar to a natural cytokine amino acid sequence so as to have cytokine activity (i.e. activity associated with naturally occurring, or wild-type cytokines). A homologue can include natural allelic variants and modified cytokines in which at least one or a few amino acids have been inserted, deleted, substituted, and/or derivatized in such a manner that such modifications do not substantially effect the ability of the cytokine homologue to function as a cytokine.

In accordance with the present invention, a cytokine includes a protein that is capable of affecting the biological function of another cell. A biological function affected by a cytokine can include, but is not limited to, cell growth, cell differentiation or cell death. Preferably, a cytokine of the present invention is capable of binding to a specific receptor on the surface of a cell, thereby affecting the biological function of a cell. Cytokines can be capable of affecting the biological function of cells, including, but not limited to, a lymphocyte, a muscle cell, a hematopoietic precursor cell, a mast cell, a natural killer cell, a macrophage, a monocyte, an epithelial cell, an endothelial cell, a dendritic cell, a mesenchymal cell, a Langerhans cell, cells found in granulomas and tumor cells of any cellular origin, and more preferably a mesenchymal cell, an epithelial cell, an endothelial cell, a muscle cell, a macrophage, a monocyte, a T cell and a dendritic cell.

Preferred cytokines for use in the present invention include: hematopoietic growth factor, an interleukin, an interferon, an immunoglobulin superfamily molecule, a tumor necrosis factor family molecule and/or a chemokine (i.e., a protein that regulates the migration and activation of cells, particularly phagocytic cells). A more preferred cytokine is an interleukin. An even more preferred cytokine is interleukin-2 (IL-2), interleukin-7 (IL-7), interleukin-12 (IL-12), interleukin-15 (IL-15), interleukin-18 (IL-18), granulocyte-macrophage colony stimulating factor (GM-CSF) and/or interferon-γ (IFNγ). A most preferred cytokine is interleukin-2 (IL-2), interleukin-12 (IL-12), interleukin-18 (IL-18), and/or interleukin-15 (IL-15).

As will be apparent to one of skill in the art, the present invention is intended to apply to cytokines derived from all types of mammals. A preferred mammal from which to derive cytokines includes a mouse, a human and a domestic pet (e.g., dog, cat). A more preferred mammal from which to derive cytokines includes a dog and a human. An even more preferred mammal from which to derive cytokines is a human. According to the present invention, a cytokine or cytokine-encoding nucleic acid molecule is preferably derived from the same species of mammal as the mammal to be treated. For example, a cytokine-encoding nucleic acid molecule derived from a canine (i.e., dog) nucleic acid molecule is preferably used to treat a disease in a canine. It is to be noted that the term "a" or "an" entity refers to one or more of that entity; for example, a cytokine refers to one or more cytokines. As such, the terms "a" (or "an"), "one or more" and "at least one" can be used interchangeably herein.

When the cytokine is provided by a nucleic acid molecule encoding the protein, the nucleic acid sequence encoding the cytokine is operatively linked to one or more transcription control sequences to form a recombinant molecule. The phrase "operatively linked" refers to linking a nucleic acid molecule to a transcription control sequence in a manner such that the molecule is able to be expressed when transfected (i.e., transformed, transduced or transfected) into a host cell. Preferably, a nucleic acid molecule encoding a cytokine for use in a composition of the present invention is operatively linked to a transcription control sequence which allows for transient expression of the molecule in the recipient mammal. To avoid adverse affects of prolonged immune activation (e.g., shock, excessive inflammation, immune tolerance), it is a preferred embodiment of the present invention that a cytokine encoded by a nucleic acid molecule be expressed in the immunized mammal for about 72 hours to about 1 month, and preferably, from about 1 week to about 1 month, and more preferably, from about 2 weeks to about 1 month. Expression of a longer period of time than 1 month is not desired in instances where undesirable effects associated with prolonged immune activation occur. However, if such effects do not occur for a particular composition or can be avoided or controlled, then extended expression is acceptable. In one embodiment, transient expression can be achieved by selection of suitable transcription control sequences, for example. Transcription control sequences which are suitable for transient gene expression are discussed below.

Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells useful in the method of the present invention. A variety of such transcription control sequences are known to those skilled in the art. Preferred transcription control sequences include those which function in mammalian, bacteria, insect cells, and preferably in mammalian cells. More preferred transcription control sequences include, but are not limited to, simian virus 40 (SV-40), β-actin, retroviral long terminal repeat (LTR), Rous sarcoma virus (RSV), cytomegalovirus (CMV), tac, lac, trp, trc, oxy-pro, omp/lpp, rrnB, bacteriophage lambda (λ) (suc as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, *Pichia* alcohol oxidase, alphavirus subgenomic promoters (such as Sindbis virus subgenomic promoters), baculovirus, *Heliothis zea* insect virus, vaccinia virus and other poxviruses, herpesvirus, and adenovirus transcription control sequences, as well as other sequences capable of controlling gene expression in eukaryotic cells. Additional suitable transcription control sequences include tissue-specific promoters and enhancers (e.g., T cell-specific enhancers and promoters). Transcription control sequences of the present invention can also include naturally occurring transcription control sequences naturally associated with a gene encoding a cytokine.

Particularly preferred transcription control sequences for use in the present invention include promoters which allow for transient expression of a nucleic acid molecule that is to be expressed, thereby allowing for expression of the cytokine encoded by the nucleic acid molecule to be terminated after a time sufficient to elicit an immune response. Adverse effects related to prolonged activation of the immune system can be avoided by selection of promoters and other transcription control factors which allow for transient expression of a nucleic acid molecule. Suitable promoters for use with nucleic acid molecules encoding cytokines for use in the present invention include cytomegalovirus (CMV) promoter and other non-retroviral virus-based promoters such as RSV promoters, adenovirus promoters and Simian virus promoters. LTR, tissue-specific promoters, promoters from self-replication viruses and papillomavirus promoters, which may be quite desirable in gene therapy/gene replacement protocols because they provide prolonged expression of a transgene, are not preferred transcription control sequences for use in the present invention.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention also contains secretory signals (i.e., signal segment nucleic acid sequences) to enable an expressed cytokine protein to be secreted from the cell that produces the protein. Suitable signal segments include: (1) a cytokine signal segment; or (2) any heterologous signal segment capable of directing the secretion of a cytokine protein according to the present invention.

It is noted that the description of recombinant production of a cytokine presented above can be readily applied to the encoding and production of any protein to be expressed by a nucleic acid molecule of the present invention.

According to the present invention, an effective administration protocol (i.e., administering a vaccine or therapeutic composition in an effective manner) comprises suitable dose parameters and modes of administration that result in elicitation of an immune response in a mammal that has a disease, preferably so that the mammal is protected from the disease. Effective dose parameters can be determined using methods standard in the art for a particular disease. Such methods include, for example, determination of survival rates, side effects (i.e., toxicity) and progression or regression of disease. In particular, the effectiveness of dose parameters of a therapeutic composition of the present invention when treating cancer can be determined by assessing response rates. Such response rates refer to the percentage of treated patients in a population of patients that respond with either partial or complete remission. Remission can be determined by, for example, measuring tumor size or microscopic examination for the presence of cancer cells in a tissue sample.

In accordance with the present invention, a suitable single dose size is a dose that is capable of eliciting an immune response in a mammal with a disease when administered one or more times over a suitable time period. Doses can vary depending upon the disease being treated. In the treatment of cancer, a suitable single dose can be dependent upon whether the cancer being treated is a primary tumor or a metastatic form of cancer. One of skill in the art can readily determine appropriate single dose sizes for systemic administration based on the size of a mammal and the route of administration. One of skill in the art can monitor the effectiveness of the immunization by measuring, for example, proliferative response, cytokine responses, cytotoxicity, antibody production, by enumerating antigen-specific T cells, or monitoring delayed type hypersensitivity (DTH) responses.

In a preferred embodiment, an appropriate single dose of the nucleic acid:liposome portion of the composition of the present invention is from about 0.1 µg to about 100 µg per kg body weight of the mammal to which the complex is being administered. In another embodiment, an appropriate single dose is from about 1 µg to about 10 µg per kg body weight. In another embodiment, an appropriate single dose of nucleic acid:lipid complex is at least about 0.1 µg of nucleic acid to the mammal, more preferably at least about 1 µg of nucleic acid, even more preferably at least about 10 µg of nucleic acid, even more preferably at least about 50 µg of nucleic acid, and even more preferably at least about 100 µg of nucleic acid to the mammal.

As discussed above, an appropriate single dose size for the composition based on the amount of immunogen is an amount of the vaccine that delivers from about 1 µg immunogen per individual mammal to about 1 mg immunogen per individual mammal, and more preferably from about 1 µg immunogen per individual mammal to about 100 µg immunogen per individual mammal, and even more preferably from about 10 µg immunogen per individual mammal to about 100 µg immunogen per individual mammal. In one embodiment, an appropriate single dose size for the composition based on the amount of immunogen is an amount of the vaccine that delivers at least about 0.1 µg immunogen per individual mammal, and more preferably at least about 1 µg immunogen per individual mammal, and m ore preferably, at least about 5 µg immunogen per individual mammal, and more preferably at least about 10 µg immunogen per individual mammal. One of skill in the art will appreciate that the dose amount will depend to some extent on the size of the mammal to which the composition is being administered.

Preferably, when the composition of the present invention contains a nucleic acid molecule encoding a cytokine which is to be expressed in the mammal, an appropriate single dose of the nucleic acid molecule encoding the cytokine results in at least about 1 pg of protein expressed per mg of total tissue protein per µ g of nucleic acid delivered; and preferably, at least about 10 pg of protein expressed per mg of total tissue protein per µ g of nucleic acid delivered; and even more preferably, at least about 50 pg of protein expressed per mg of total tissue protein per µ g of nucleic acid delivered; and most preferably, at least about 100 pg of protein expressed per mg of total tissue protein per µ g of nucleic acid delivered.

A suitable single dose of a vaccine or therapeutic composition of the present invention to elicit a systemic, immunogen-specific immune response in a mammal is an amount that, when administered by any route of administration, elicits a cellular and/or humoral immune response in vivo in a mammal, as compared to a mammal which has not been administered with the therapeutic composition of the present invention (i.e., a control mammal).

A suitable single dose of a vaccine or therapeutic composition to elicit an immune response against a tumor is an amount that is sufficient to reduce, stop the growth of, and preferably eliminate, the tumor following administration of the composition into the tissue of the mammal that has cancer. A single dose of a vaccine or therapeutic composition useful to elicit an immune response against an infectious disease and/or against a lesion associated with such a disease is substantially similar to those doses used to treat a tumor, wherein the amount is sufficient to reduce, eliminate, or prevent at least one symptom of an infectious disease or lesion associated with such disease. Similarly, a single dose of a therapeutic composition useful to elicit an immune response against an allergen is substantially similar to those doses used to treat a tumor, wherein the amount is sufficient to reduce, eliminate or prevent at least one symptom of allergic inflammation. Also, a single dose of a therapeutic composition useful to elicit an immune response against a self-antigen is substantially similar to those doses used to treat a tumor, wherein the amount is sufficient produce a desired therapeutic effect in the mammal as a result of eliciting an immune response against the self-antigen.

It will be obvious to one of skill in the art that the number of doses administered to a mammal is dependent upon the extent of the disease and the response of an individual patient to the treatment. For example, a large tumor may require more doses than a smaller tumor. In some cases, however, a patient having a large tumor may require fewer doses than a patient with a smaller tumor, if the patient with the large tumor responds more favorably to the therapeutic composition than the patient with the smaller tumor. Thus, it is within the scope of the present invention that a suitable number of doses includes any number required to treat a given disease.

It is to be noted that the method of the present invention further differs from previously described gene therapy/gene replacement protocols, because the time between administration and boosting of the nucleic acid:lipid complex is significantly longer than the typical administration protocol for gene therapy/gene replacement. For example, elicitation of an immune response using the compositions and methods of the present invention typically includes an initial administration of the therapeutic composition, followed by booster immunizations at 2-4 weeks after the initial administration, optionally followed by subsequent booster immunizations every 2-4 weeks after the first booster, as needed to treat a disease according to the present invention. In contrast, gene therapy/gene replacement protocols typically require more frequent administration of a nucleic acid in order to obtain sufficient gene expression to generate or replace the desired gene function (e.g., weekly administrations).

A preferred number of doses of a vaccine or therapeutic composition of the present invention is from about 2 to about 10 administrations patient, more preferably from about 3 to about 8 administrations per patient, and even more preferably from about 3 to about 7 administrations per patient. Preferably, such administrations are given once every 2-4 weeks, as described above, until signs of a therapeutic improvement appear, and then once a month until the disease is gone, or until sufficient memory immune response is established to be considered to be effective for prevention of the disease or condition. Variation of the dose and frequency of administration can be determined by those of skill in the art, and will depend on the immunogen being administered, the type of condition being targeted, and whether prevention or treatment of the condition is desired.

As discussed above, a vaccine or therapeutic composition of the present invention is administered to a mammal in a manner effective to deliver the composition to a cell, a tissue, and/or systemically to the mammal, whereby elicitation of an immunogen-specific immune response is achieved as a result of the administration of the composition. It is noted that it is not necessary to specifically target the composition to a particular cell or tissue, since the inventors have found that several different modes of administration in the absence of specific targeting is effective to elicit the desired immune response. Suitable administration protocols include any in vivo or ex vivo administration protocol. According to the present invention, suitable methods of administering a vaccine or therapeutic composition of the present invention to a patient include any route of in vivo administration that is suitable for delivering the composition into a patient. The preferred routes of administration will be apparent to those of skill in the art, depending on the type of condition to be prevented or treated, the immunogen used, and/or the target cell population. Preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue. In particular, any routes of delivery which elicit an immune response in the mucosal tissues is preferred. Such routes include bronchial, intradermal, intramuscular, intranasal, other inhalatory, rectal, subcutaneous, topical, transdermal, vaginal and urethral routes. Some particularly preferred routes of administration include, intravenous, intraperitoneal, subcutaneous, intradermal, intranodal, intramuscular, transdermal, inhaled, intranasal, rectal, vaginal, urethral, topical, oral, intraocular, intraarticular, intracranial, and intraspinal. As discussed previously, combinations of routes of delivery can be used and in some instances, may enhance the therapeutic effects of the vaccine or composition. Therefore, any combination of two or more routes of administration, performed simultaneously, within a short time period one after another, or at different time intervals relative to the immunization schedule (e.g., initial administration versus boosters), are contemplated by the present inventors. In one embodiment, a preferred route of administration is a combination of any one or more of intravenous, intraperitoneal or intradermal administration with intranodal administration. In another embodiment where the target cells are in or near a tumor, a preferred route of administration is by direct injection into the tumor or tissue surrounding the tumor.

Ex vivo administration refers to performing part of the regulatory step outside of the patient, such as administering a composition of the present invention to a population of cells removed from a patient under conditions such that the composition contacts and/or enters the cell, and returning the lipofected cells to the patient. Ex vivo methods are particularly suitable when the target cell can easily be removed from and returned to the patient.

Many of the above-described routes of administration, including intravenous, intraperitoneal, intradermal, and intramuscular administrations can be performed using methods standard in the art. Aerosol (inhalation) delivery can also be performed using methods standard in the art (see, for example, Stribling et al., Proc. Natl. Acad. Sci. USA 189: 11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. One method of local administration is by direct injection; Direct injection techniques are particularly useful for administering a composition to a cell or tissue that is accessible by surgery, and particularly, on or near the surface of the body. Administration of a composition locally within the area of a target cell refers to injecting the composition centimeters and preferably, millimeters from the target cell or tissue. Suitable sites for administration include sites in which the target site for immune activation is not restricted to the first organ having a capillary bed proximal to the site of administration (i.e., compositions can be administered at an administration site that is distal to the target immunization site). In other words, for example, intravenous administration of a composition of the present invention which is used to treat a kidney tumor in a mammal can be administered intravenously at any site in the mammal and will still elicit a strong anti-tumor immune response and be efficacious at reducing or eliminating the tumor, even though the kidney is not the first organ having a capillary bed proximal to the site of administration.

In the method of the present invention, vaccines and therapeutic compositions can be administered to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, sheep, cattle, horses and pigs, with humans and dogs being particularly preferred, and humans being most preferred. While a therapeutic composition of the present invention is effective to elicit an immune response against a disease in inbred species of mammals, the composition is particularly useful for eliciting an immune response in outbred species of mammals. As shown in the Examples, the method of the present invention can be readily translated to large animal spontaneous disease models, including dogs and cats. Thus, the effectiveness of lipid-DNA-antigen vaccines is not restricted to any one species of animal and is predicted to be effective in humans.

As discussed above, a vaccine or therapeutic composition of the present invention administered by the present method is useful for eliciting an immune response in a mammal having a variety of diseases, and particularly cancer, allergic inflammation and infectious diseases, as well as diseases that can be ameliorated by elicitation of an immune response against a self-antigen.

A therapeutic composition of the present invention is advantageous for eliciting an immune response in a mammal that has cancer in that the composition overcomes the mechanisms by which cancer cells avoid immune elimination (i.e., by which cancer cells avoid the immune response effected by the mammal in response to the disease). Cancer cells can avoid immune elimination by, for example, being only slightly immunogenic, modulating cell surface antigens and inducing immune suppression. A suitable therapeutic composition for use in eliciting an immune response in a mammal that has cancer comprises an immunogen useful for eliciting an immune response against the cancer, including individual tumor antigens or epitopes, tumor lysates, or whole tumor cells, and any combinations thereof. The immunogen(s) can be derived from autologous tumors or tumor antigens, from allogeneic tumors or tumor antigens, from xenogenic tumors or tumor antigens, or combinations thereof. Multiple different types of tumors may also serve as the source for the immunogens. The composition further comprises a liposome and a nucleic acid molecule that does not encode the immunogen. A therapeutic composition of the present invention, elicits a systemic, immunogen-specific immune response in the mammal and in particular, activates cytotoxic T cells, natural killer cells, T helper cells and macrophages, as well as humoral immunity. Such cellular activation overcomes the otherwise relative lack of immune response to cancer cells, leading to the destruction of such cells.

A therapeutic composition of the present invention which includes an immunogen that elicits an immune response against a tumor is useful for eliciting an immune response in a mammal that has cancer, including both primary tumors and metastatic forms of cancer. Treatment with the therapeutic composition overcomes the disadvantages of traditional treatments for metastatic cancers. For example, compositions of the present invention can target dispersed metastatic cancer cells that cannot be treated using surgical methods. In addition, administration of such compositions do not result in the harmful side effects caused by chemotherapy and radiation therapy, and can be administered repeatedly. Moreover, the compositions administered by the method of the present invention typically elicit a powerful immune response such that delivery of the composition at least in the vicinity of the target site (at or adjacent to the site) provides effective immune activation and efficacy against the target.

Cancers to be treated or prevented using the method and composition of the present invention include, but are not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias, and metastatic cancers thereof. Particularly preferred cancers to treat with a therapeutic composition of the present invention include primary lung cancers and pulmonary metastatic cancers. A therapeutic composition of the present invention is useful for eliciting an immune response in a mammal to treat tumors that can form in such cancers, including malignant and benign tumors. Preferably, expression of the tumor antigen in a tissue of a mammal that has cancer produces a result selected from the group of alleviation of the cancer, reduction of a tumor associated with the cancer, elimination of a tumor associated with the cancer, prevention of metastatic cancer, prevention of the cancer and stimulation of effector cell immunity against the cancer.

A vaccine or therapeutic composition of the present invention which includes an immunogen that is associated with an infectious disease (e.g., from a pathogenic microorganism that causes the disease) is advantageous for eliciting an immune response in a mammal that has an infectious disease that is beneficially effected by an immune response or to elicit an immune response in a mammal that will protect the mammal against subsequent infection by the pathogen. An infectious disease responsive to an immune response is a disease caused by a pathogen in which the elicitation of an immune response against the pathogen can result in a prophylactic or therapeutic effect as previously described herein. Such a method provides a long term, targeted therapy for primary lesions (e.g., granulomas) resulting from the propagation of a pathogen. As used herein, the term "lesion" refers to a lesion formed by infection of a mammal with a pathogen. The infectious disease can be either chronic or acute. A therapeutic composition for use in the elicitation of an immune response in a mammal that has an infectious disease comprises an immunogen that is selected from an antigen from a pathogen, an immunogenic epitope from a pathogen, a whole pathogen organism, or a lysate or other fraction of a pathogen organism, a secreted toxin or a spore from the pathogen, or any combination thereof. Immunogens derived from different strains of the same or similar pathogens, or from different pathogens may be combined. The composition further comprises a liposome and a nucleic acid molecule that does not encode the immunogen against the pathogen. Similar to the mechanism described above for the treatment of cancer, eliciting an immune response in a mammal that has an infectious disease with immunogens from the infectious disease pathogens can result in increased T cell, natural killer cell, macrophage cell activity and humoral immune responses that overcome the relative lack of immune response to a lesion formed by a pathogen. Preferably, delivery of the immunogen to a tissue of a mammal that has an infectious disease produces a result which includes alleviation of the disease, regression of established lesions associated with the disease, alleviation of symptoms of the disease, immunization against the disease and/or stimulation of effector cell immunity against the disease.

Pathogens from which immunogens useful in the present invention can be derived include, but are not limited to, bacteria (including intracellular bacteria which reside in host cells), viruses, parasites (including internal parasites), fungi (including pathogenic fungi), endoparasites, ectoparasites, and prions (e.g., bovine spongiform encephalopathy; BSE). Preferred infectious diseases to treat or prevent with a vaccine or therapeutic composition of the present invention include chronic infectious diseases, including pulmonary infectious diseases, such as tuberculosis. Particularly preferred infectious diseases to treat with a therapeutic composition of the present invention include viral infections such as those caused by human immunodeficiency virus, Epstein Barr virus, other Herpes viruses, papilloma virus, and Hepatitis viruses; mycobacterial infections such as that caused by *Mycobacterium tuberculosis*, and; fungal infections such as those caused by *Candida, Blastomyces*, and *Histoplasma*; parasitic infections such as those caused by *Toxoplasma*; and bacterial infectious diseases such as those caused by *Cryptococcus, Bacillus anthracis* and *Yersenia pestis, Staphylococcus, Pseudomonas, Streptococcus, Enterococcus, Salmonella, Pasteurella, Fransicella* and other gram negative and gram positive bacterial pathogens.

A therapeutic composition of the present invention which includes an immunogen that elicits an immune response against an allergen is advantageous for eliciting an immune response in a mammal that has or is at risk of developing a disease associated with allergic inflammation. A disease associated with allergic inflammation is a disease in which the elicitation of one type of immune response (e.g., a Th2-type immune response) against a sensitizing agent, such as an allergens can result in the release of inflammatory mediators that recruit cells involved in inflammation in a mammal, the presence of which can lead to tissue damage and sometimes death. The method of the present invention typically elicits a Th1-type response, which, without being bound by theory, the present inventors believe can have prophylactic or therapeutic effects such that allergic inflammation is alleviated or reduced. A therapeutic composition for use in the elicitation of an immune response in a mammal that has a disease associated with allergic inflammation comprises an immunogen that is an allergen, an immunogenic portion of an allergen, an epitope of an allergen, or combinations thereof. The composition can include multiple allergens, portions thereof, epitopes thereof, or combinations of the same. The composition further comprises a liposome and a nucleic acid molecule that does not encode an immunogen that elicits an immune response against the target allergen(s). Similar to the mechanism described above for the treatment of cancer, eliciting an immune response in a mammal that has a disease associated with allergic inflammation can result in increased Th1-type T cell, natural killer cell, or macrophage cell activity or humoral immune responses, that overcome the harmful effects of a Th2-type immune response against the same allergen. Preferably, delivery of the allergen to a tissue of a mammal that has a disease associated with allergic inflammation or is at risk of developing the disease, produces a result which includes alleviation of the disease, alleviation of symptoms of the disease, desensitization against the disease and stimulation a protective immune response against the disease. Preferred diseases associated with allergic inflammation which are preferable to treat using the method and composition of the present invention include, allergic airway diseases, allergic rhinitis, allergic conjunctivitis and food allergy. Vaccines comprising allergen immunogens are, in one embodiment, administered by a route including aerosol, intranasal, subcutaneous, intramuscular, or oral administration.

A therapeutic composition of the present invention which includes an immunogen that elicits an immune response against a self-antigen is advantageous for eliciting an immune response in a mammal that has or is at risk of developing a disease wherein an immune response against such an antigen will have a therapeutic benefit in the patient. For example, in conditions where abnormal blood vessel growth is experienced, the present invention can be used to immunize the patient against an angiogenic growth factor or receptor thereof, such as the VEGF receptor. As another example, immunization against a signaling molecule is used to treat a neurologic disease. As yet another example, immunization against an endothelial cell or a fraction thereof is used to treat cancer. Such immunogens include proteins, portions thereof, carbohydrates, lipid molecules, normal cells (e.g., non-tumor cells) and fractions thereof.

The following examples are provided for the purposes of illustration and are not intended to limit the scope of the present invention.

EXAMPLES

Example 1

The following example shows that immunization with cationic lipid-DNA complexes combined with tumor lysates generates antitumor immunity.

The ability of cationic lipid-DNA complexes (CLDC) to enhance the effectiveness of vaccination with tumor antigens was assessed in BALB/c mice using the syngeneic CT26 tumor cell line. The cationic lipid-DNA complexes were prepared using DOTIM and cholesterol liposomes and empty vector (EV; non-coding) plasmid DNA. The tumor cell vaccine consisted of lysates of CT26 tumor cells, which were prepared by first incubating live tumor cells in vitro with EV/CLDC for 30 minutes, then subjecting the cells to 4 freeze-thaw cycles. The tumor lysate solution was then added to 1 ml of pre-formed EV/CLDC to prepare lipid-antigen-DNA complexes (LADC), where the antigen was comprised of tumor cell lysates. Control tumor cell lysates were prepared by freeze-thaw of tumor cells without addition of any EV/CLDC. BALB/c mice (4 per group) were immunized with either: (1) control tumor cell lysates only ("cells"; equivalent to $10^6$ tumor cells per mouse); (2) 10 μg EV/CLDC only ("CLDC"); or (3) the tumor vaccine ("Vacc"), which consisted of tumor lysates plus 10 μg EV/CLDC. Untreated mice served as controls. Mice were boosted once 7 days later, then spleen cells were collected 7 days after that and re-stimulated in vitro with autologous tumor cell lysates.

Twenty-four hours later, release of IFN-γ into tissue culture supernatants was quantitated by specific ELISA assay (FIG. 1). Immunization with the tumor lysate vaccine elicited significantly greater release of IFN-γ than did immunization with tumor lysates only or with CLDC only. These data indicate that EV/CLDC have potent adjuvant activity when combined with tumor antigens and can generate substantial antitumor immunity against even syngeneic tumors.

Example 2

The following example demonstrates that immunization with a CLDC plus tumor lysates elicits high levels of cytotoxic T lymphocyte (CTL) activity.

Figure 2:
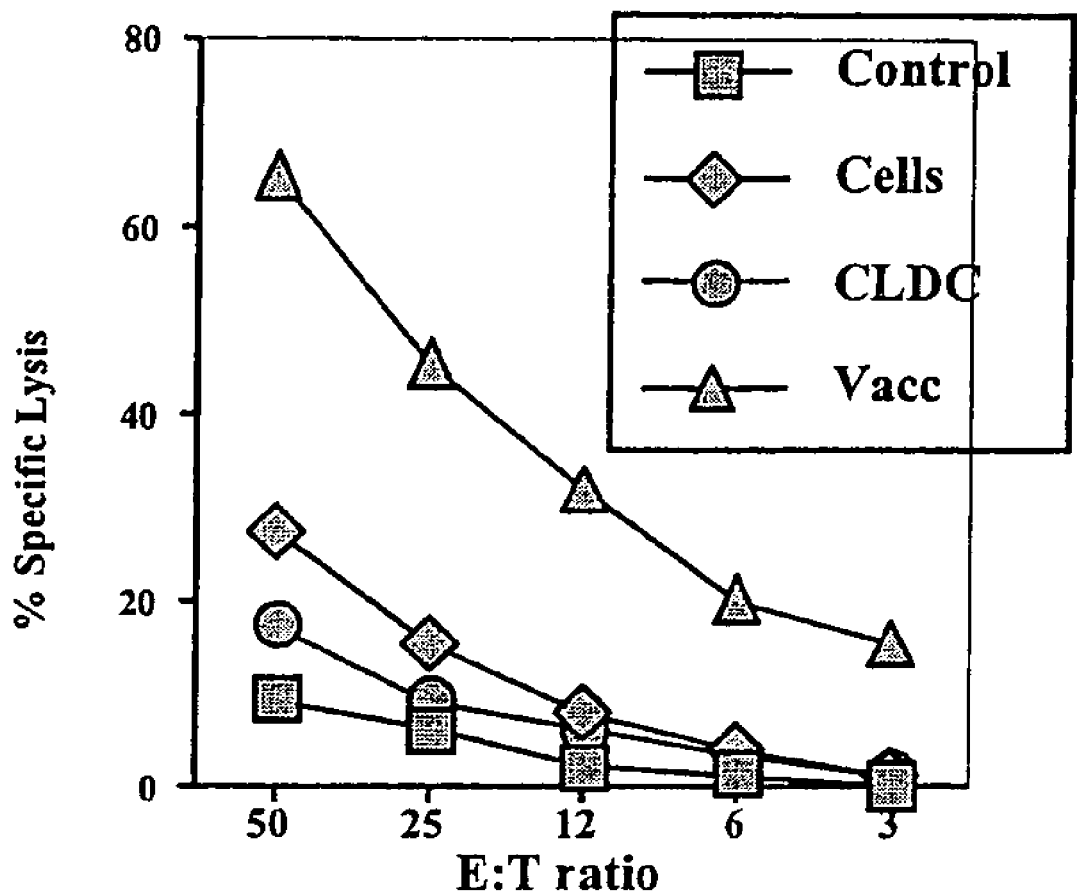
FIG. 2 is a line graph showing that immunization with a CLDC plus tumor lysates elicits high levels of CTL activity.
Figure 3:
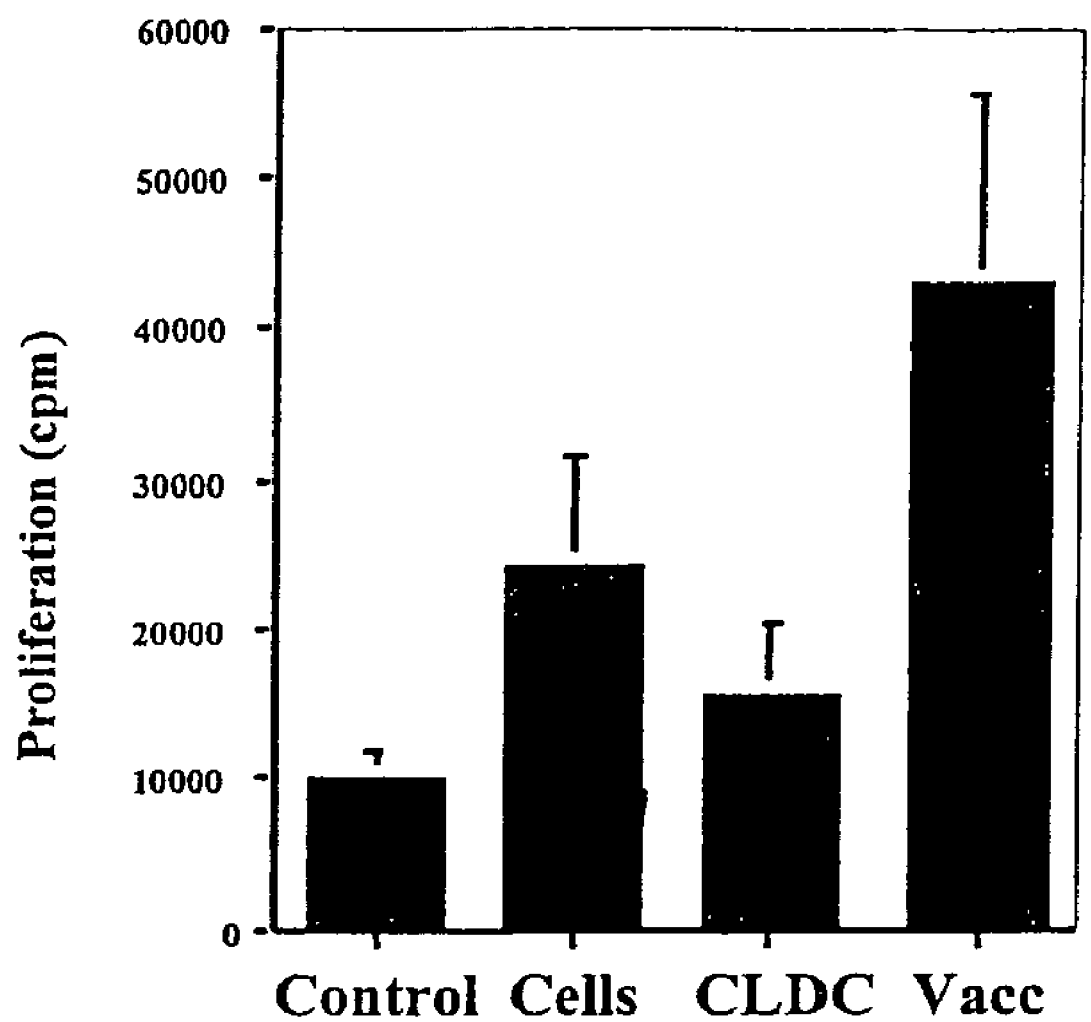
FIG. 3 is a bar graph showing that immunization with tumor lysates combined with CLDC elicits lymphocyte proliferative activity.

The effect of tumor vaccination on tumor-specific cytotoxic T lymphocyte activity (CTL) was assessed using BALB/c mice and the CT26 tumor line, as described in Example 1 above. BALB/c mice (4 per group) were immunized twice with either tumor lysates only ("cells"), with EV/CLDC only ("CLDC"), or with tumor lysates plus CLDC ("Vacc"). Untreated mice served as controls. One week after the second immunization, spleen cells were harvested and re-stimulated in vitro for 5 days using irradiated CT26 cells. On day 5, cytotoxic activity of the-effector T cells was assessed using CT26 $^{51}$Cr-labeled target cells. As shown in FIG. 2, vaccination with tumor lysates plus CLDC elicited much greater levels of CTL activity against autologous tumor cells than immunization with either tumor lysates alone or CLDC alone.

Example 3

The following example demonstrates that immunization with tumor lysates combined with CLDC elicits lymphocyte proliferative activity.

BALB/c mice were immunized with either CT26 tumor lysates alone ("cells"), CLDC alone, or tumor lysates plus CLDC ("Vacc"), as described in Example 1. One week after a booster vaccination, spleen cells were harvested and incubated with tumor cell lysates for 3 days. The proliferative response was assessed by pulsing with $^3$H thymidine for 18 h. The mean proliferative response (±SE) was then plotted. Immunization with tumor lysates plus CLDC elicited significantly greater proliferative responses than immunization with tumor lysates alone. These results and the results from Example 2 (FIG. 2) indicate that a tumor vaccine prepared using tumor lysates combined with CLDC is capable of eliciting both CD4+ T cell responses (proliferation) and CD8+ T cell responses (CTL activity).

Example 4

The following example shows that tumor vaccination inhibits the growth of established lung tumor metastases.

Figure 4:
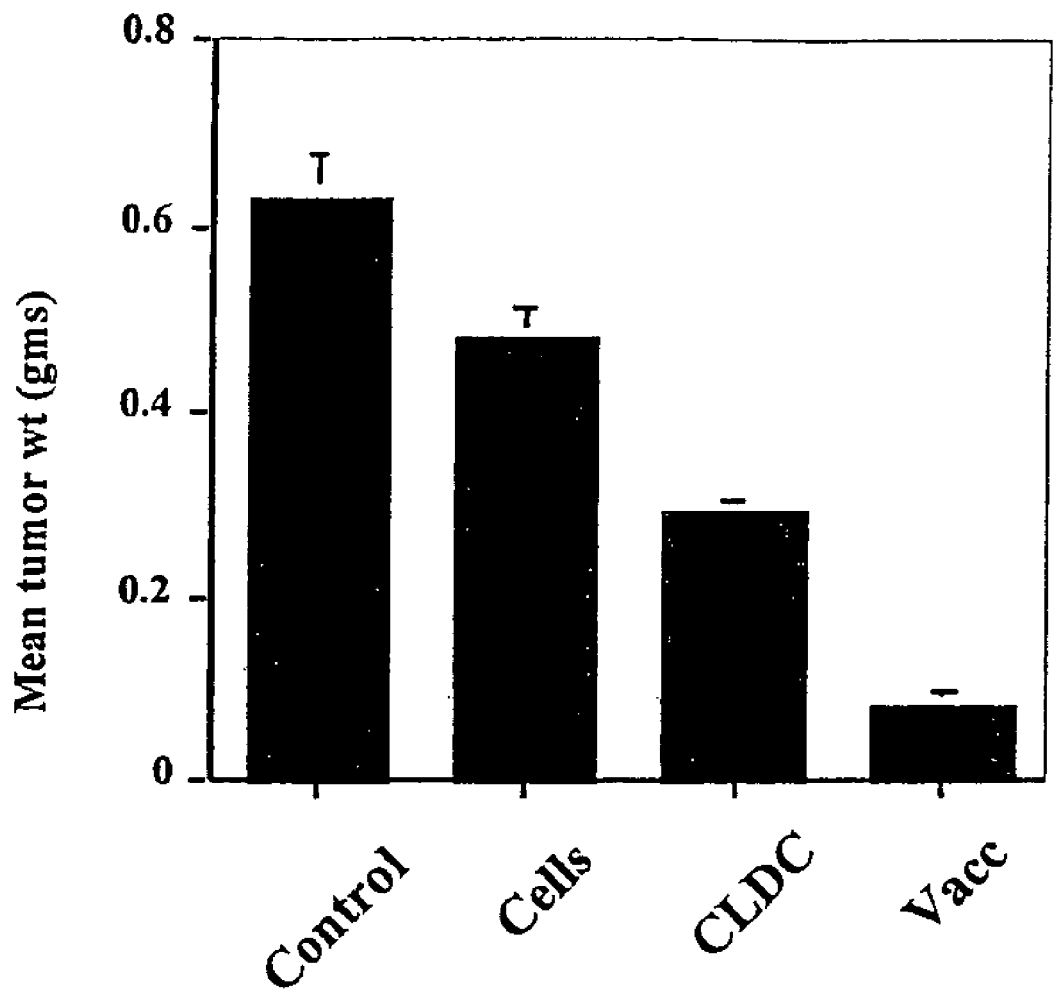
FIG. 4 is a bar graph showing that tumor vaccination inhibits the growth of established lung tumor metastases.

BALB/c mice (5 per group) with day 3 established CT26 lung metastases were treated by vaccination with tumor lysates only ("cells"), CLDC only, or tumor lysates plus CLDC ("Vacc"), administered intravenously, as described in Example 1. The vaccination was repeated twice at 7-day intervals. Five days later, the mice were sacrificed and the lung tumor burden was determined by determining the weight of lung tumor nodules (lung weight minus weight of normal control lungs). As shown in FIG. 4, therapeutic vaccination with tumor lysates plus CLDC induced a significantly greater reduction in lung tumor burden than either tumor cell lysates alone or CLDC alone. These results demonstrate that the combination of CLDC plus tumor antigens creates a potent vaccine for generating therapeutic antitumor immunity.

Example 5

This example demonstrates that vaccination with autologous tumor lysates using LADC induces CTL activity in dogs with osteosarcoma.

Figure 5A:
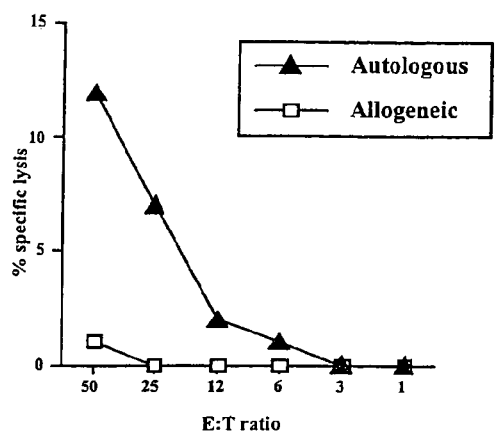
FIGS. 5A-5B are line graphs showing that vaccination with autologous tumor lysates using lipid-antigen-DNA complex (LADC) induces CTL activity in a dogs with osteosarcoma (FIGS. 5A and 5B each represent a different dog).
Figure 5B:
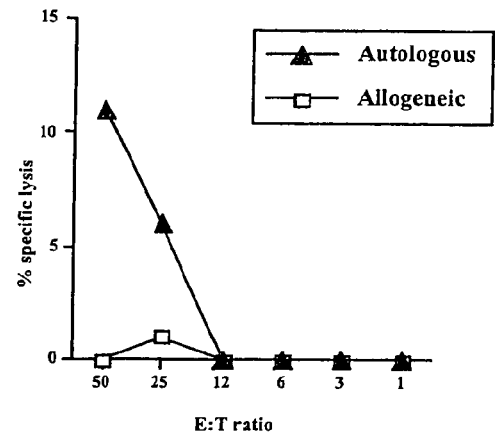

The ability of lipid-antigen-DNA complexes (LADC) to elicit antitumor immunity was investigated in dogs with spontaneous osteosarcoma. Tumor lysates and primary cultures of the tumor tissues were prepared from tumor tissues immediately after amputation of the limb for control of the primary tumor (osteosarcoma). The tumor lysates were then added to CLDC to form LADC. In addition to tumor lysates, a second antigen KLH (keyhole limpet hemocyanin) was also added to the LADC vaccine. Each dog was immunized intravenously with LADC once every other week for 6 treatments. Peripheral blood mononuclear cells were collected after 3 immunizations, restimulated in vitro with irradiated autologous tumor cells for 5 days, then assayed for their ability to lyse autologous tumor cells or MHC and tissue-type mismatched (melanoma) tumor cells ("allogeneic"), using a chromium release assay. PBMC from both patients (FIGS. 5A and 5B, each representing a single patient) demonstrated increased CTL activity (specific lysis) against autologous tumor cells, whereas there was little killing of allogeneic target cells. These results indicate that LADC vaccination using autologous tumor lysates can generate antitumor immunity in a large animal model of spontaneous neoplasia.

Example 6

This example demonstrates that immunization with LADC by different routes elicits large numbers of antigen-specific CD8+ T cells.

Mice were immunized twice, 7 days apart, with liposome-antigen-DNA complexes (LADC) comprised of empty vector/CLDC (EV/CLDC) and a peptide (SIINFEKL) (SEQ ID NO:1) derived from ovalbumin. Each mouse received 5 μg peptide per immunization. The T cell response to LADC vaccination was assessed using MHC-peptide tetramers and flow cytometry. Spleen cells were harvested after the second immunization and stained with soluble H-2Kb molecules bound to the peptide SIINFEKL. The MHC-peptide tetrameric complexes bind specifically only to T cells expressing a T cell receptor that recognizes the SIINFEKL peptide. This technique allows direct and accurate quantitation of the exact number of antigen-specific T cells in vivo, without the need for cell culture or other manipulations. The effect of immunization by different routes (subcutaneous {SC vacc}, FIG. 6B; intravenous {IV vacc}, FIG. 6C; and intraperitoneal {IP vacc}, FIG. 6D) was also assessed. The percentage of tetramer+T cells ("tet+"; upper right quadrant of each figure) was calculated as a percentage of total CD8+ T cells in the spleen. FIGS. 6A-6D show that, compared to unvaccinated animals, animals that were immunized with LADC had a significant increase in the percentage of tet+T cells. The results indicate that vaccination using LADC can elicit large numbers of antigen-specific CD8+ T cells, even using low doses of peptide antigens. The intraperitoneal route of immunization (FIG. 6D) was particularly effective in eliciting T cell responses.

Example 7

The following example shows that immunization with peptide-pulsed dendritic cells fails to elicit strong T cell responses.

Figures 7A, 7B:
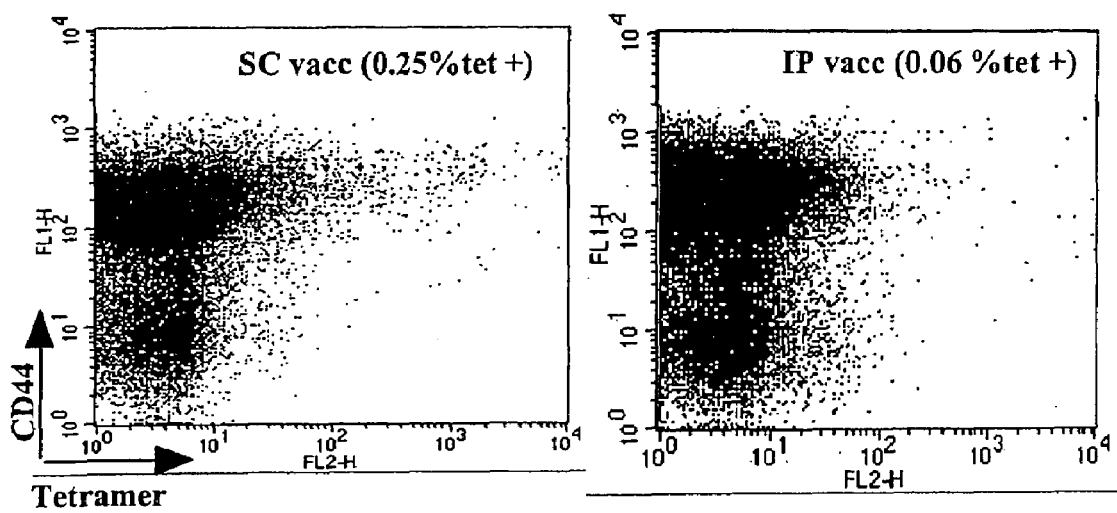
FIGS. 7A-7B are plots showing that immunization with peptide-pulsed dendritic cells by subcutaneous (FIG. 7A) or intraperitoneal (FIG. 7B) routes fails to elicit strong T cell responses.

The inventors compared the effectiveness of LADC immunization with other standard immunization techniques, including immunization with peptide in Freund's adjuvant, immunization with a vaccinia virus vector, and immunization with peptide-pulsed dendritic cells. Dendritic cell immunization is considered currently to be the most effective means of eliciting T cell immunity. Mice (3 per group) were immunized with $5 \times 10^5$ dendritic cells pulsed with SIINFEKL (SEQ ID NO:1) peptide twice, one week apart. One group of mice was immunized by the SC route (FIG. 7A) and one group by the IP route (FIG. 7B). Spleen cells were immunostained with Kb tetramers, as described in Example 6. The results demonstrate that dendritic cell immunization by either route elicited only small increases in numbers of antigen-specific CD8+ T cells, and was much less effective than LADC immunization. Moreover, immunization using peptide in Freund's adjuvant or vaccinia virus was also much less effective than LADC immunization (data not shown). Thus, LADC immunization was much more effective in eliciting strong T cell responses than any of the currently available techniques for immunization against peptide or protein antigens.

Example 8

The following example demonstrates that LADC immunization also elicits CD8+ T cell responses against weak antigens.

Figure 8A:
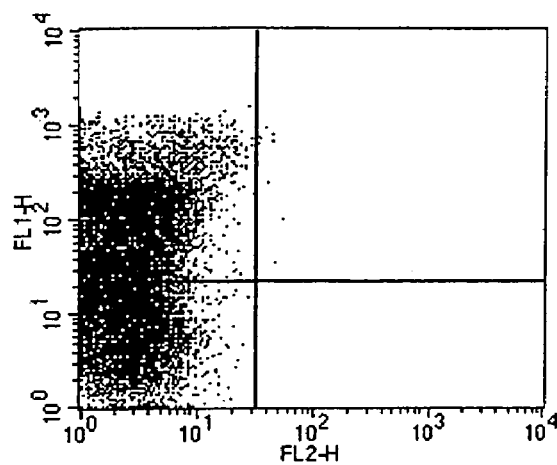
FIGS. 8A-8B are plots showing that LADC immunization also elicits CD8+ T cell responses against weak antigens.
Figure 8B:
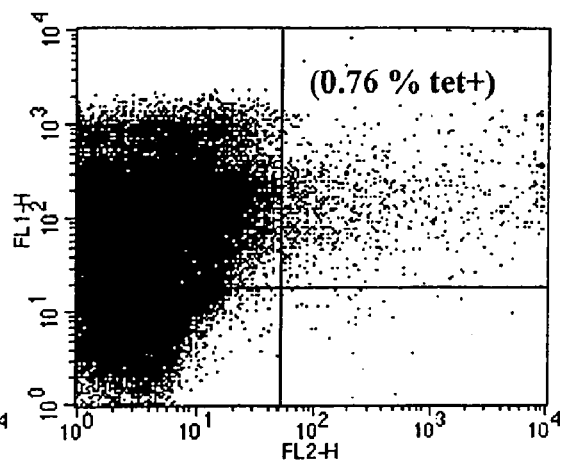

Most tumor antigens that have been identified to date are actually normal or "self" antigens. These antigens are therefore difficult to immunize against because the immune system is tolerant to these antigens. They are therefore considered to be "weak" antigens. The inventors therefore assessed the ability of LADC immunization to induce immune responses against an endogenous tumor antigen (tyrosinase-related protein 2, or trp-2). It has been difficult in the past to immunize against trp-2 using conventional vaccine approaches. Mice were immunized twice with 1 μg trp-2 peptide using LADC. T cell responses were assessed using Kb-trp-2 tetramers and flow cytometry. Compared to unvaccinated control mice (FIG. 8A), mice immunized with LADC+trp2 (FIG. 8B) had a significant increase in the percentage and number of trp2+ CD8+ T cells in the spleen. Thus, LADC immunization is sufficiently potent to elicit T cell responses against both foreign antigens (e.g., ovalbumin) and endogenous tumor antigens such as trp-2.

Example 9

The following example shows that LADC immunization also induces strong CD8+ T cell responses against protein antigens.

Figures 9A, 9B:
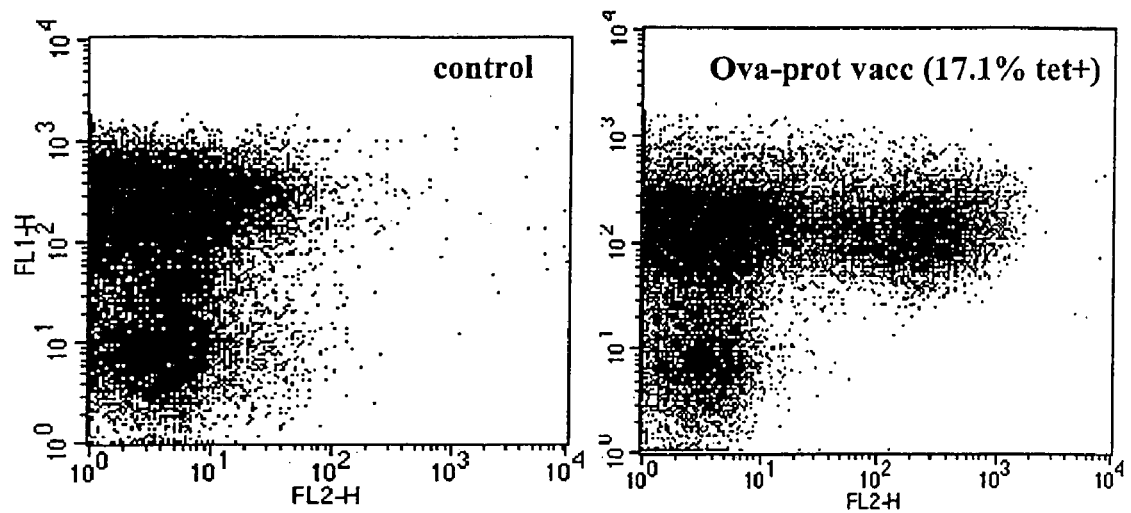
FIGS. 9A-9B are plots showing that LADC immunization also induces strong CD8+ T cell responses against protein antigens.

A major goal for vaccines against viruses, tumors, and intracellular bacterial infections is induction of CD8+ T cell responses, in addition to antibody and CD4+ T cell responses. Because of the nature of antigen processing and presentation, it is very difficult to immunize against protein antigens and elicit CD8+ T cell responses. The inventors therefore assessed the ability of LADC to introduce antigens into a class I MHC pathway and elicit CD8+ T cell responses. Mice were immunized against the ovalbumin (Ova) protein using LADC (5 μg Ova per mouse) and the CD8+ T cell response was quantitated in spleen cells and lymph nodes using tetramers (see Example 6). It was found, unexpectedly, that LADC were capable of eliciting very strong antigen-specific CD8+ T cell responses against SIINFEKL (the dominant Ova peptide; SEQ ID NO:1) following LADC immunization (FIG. 9B). In fact, the response to protein vaccination was in many cases superior to that elicited by peptide immunization (e.g., see Example 6 and FIG. 6). In contrast, immunization using dendritic cells pulsed with Ova protein did not elicit any detectable CD8+ T cell responses (data not shown). Thus, the LADC vaccine approach is particularly effective in eliciting CD8+ T cell responses not only against peptides but also against whole proteins. This is very important from the standpoint of vaccine development because it is much easier to prepare vaccines using whole proteins than to use peptide antigens.

Example 10

The following example shows that LADC efficiently introduce protein antigens into a class I MHC pathway for presentation to CD8+ T cells.

Figure 10:
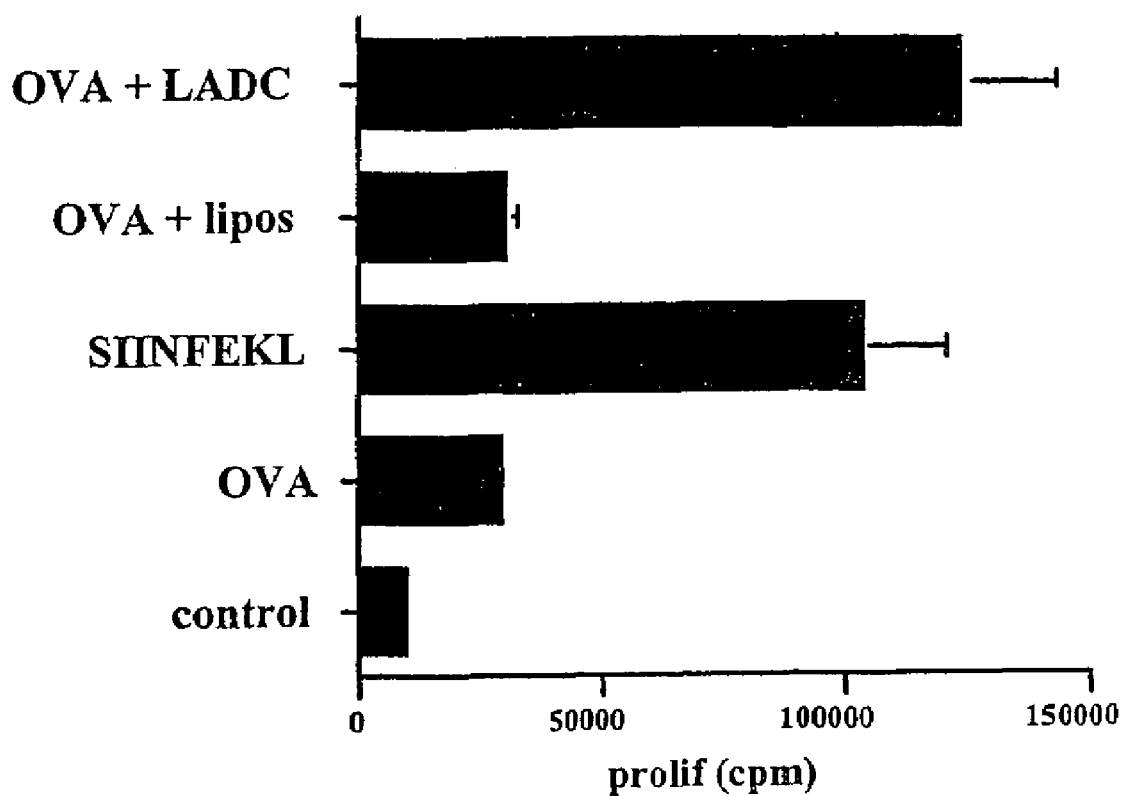
FIG. 10 is a bar graph showing that LADC efficiently introduce protein antigens into a class I MHC pathway for presentation to CD8+ T cells.

The ability to introduce protein antigens into an MHC class I pathway represents a very desirable attribute for a vaccine. The inventors therefore assessed the ability of LADC to introduce antigens into a class I pathway in vitro. EL-4 cells were incubated with the Ova protein at a concentration of 1 µg/ml in vitro for 3 h. EL-4 cells were incubated with either oval-bumin protein alone (OVA), ovalbunin in liposomes alone (OVA+lipos), or ovalbumin in LADC (OVA+LADC). Cells incubated with the SIINFEKL peptide alone (SEQ ID NO:1) served as a positive control, while EL-4 cells incubated with nothing served as a negative control. After incubation, the cells were washed, then irradiated for 30 minutes. Lymph node T cells were obtained from a mouse that was transgenic for the T cell receptor that recognizes SIINFEKL (these T cells respond by vigorous proliferation when pulsed with the SIINFEKL peptide). These T cells were then added in triplicate cultures to the EL-4 cells incubated with Ova. After 48 hours of culture, proliferation was assessed by pulsing with 3H thymidine. As shown in FIG. 10, strong proliferation was elicited by pulsing with SIINFEKL (positive control) and also by pulsing with Ova in LADC, but not by Ova alone or by Ova with liposomes alone. Thus, LADC appear to be uniquely effective in efficiently introducing protein antigens into a MHC class I pathway for antigen presentation to CD8+ T cells. This responses also occurs efficiently in vivo, as demonstrated by the results presented in Example 9 (FIG. 9).

Example 11

The following example shows that liposome-DNA complexes, and not liposomes or DNA alone, are required for effective immunization.

Figure 11A:
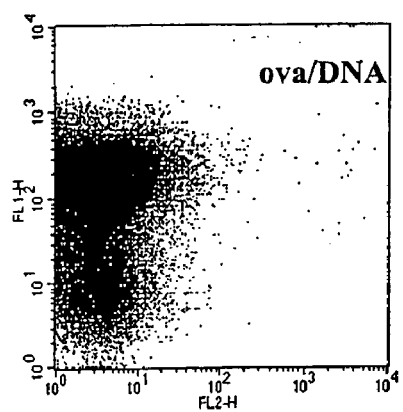
FIGS. 11A-11C are plots showing that liposome-DNA complexes, and not liposomes or DNA alone, are required for effective immunization.
Figure 11B:
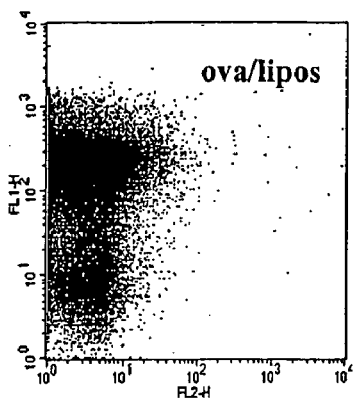
Figure 11C:
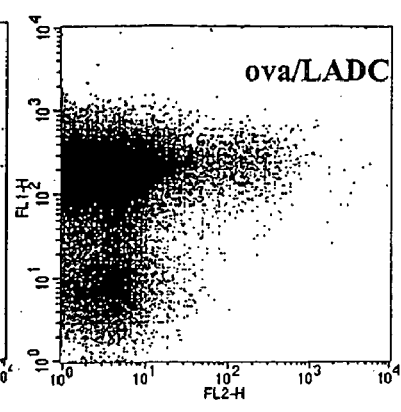

The inventors conducted experiments to determine whether the liposome and DNA complex was necessary for efficient induction of T cell responses, or whether immunization with antigen plus liposomes alone or antigen plus bacterial DNA alone could also produce effective immunization. Mice (3 per group) were immunized twice intraperitoneally with ova (5 µg per mouse) plus empty vector (EV) plasmid DNA alone (FIG. 11A), ova plus liposomes alone (FIG. 11B), or ova plus liposomes and DNA (LADC, FIG. 11C). Spleen cells were then collected and immunostained to quantitate antigen-specific CD8+ T cell responses, using Kb-SIINFEKL tetramers, as described in Example 6. The inventors found that only the combination of liposomes, DNA, and antigen was able to elicit effective T cells responses. These results were also confirmed using functional T cell assays (cytokine release and cytotoxicity; data not shown). Thus, the synergistic immune stimulatory activity of liposomes plus DNA is required for effective immunization using liposomes and DNA as vaccine adjuvants.

Example 12

Figure 12A:
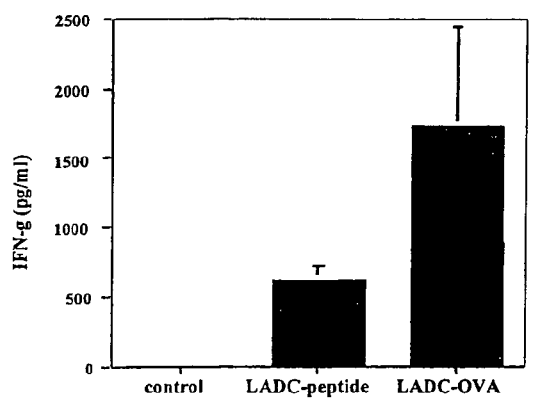
FIGS. 12A-12B are bar graphs showing that immunization using LADC elicits functional activation of T cells and production of IFN-γ.
Figure 12B:
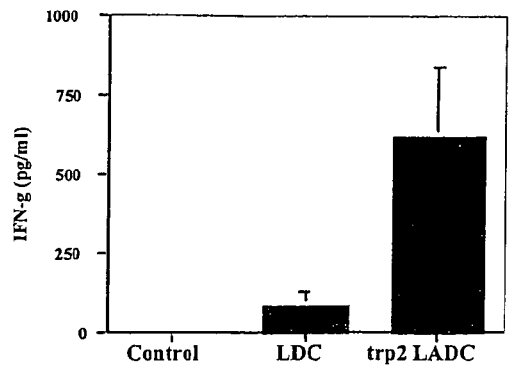
Figure 13A:
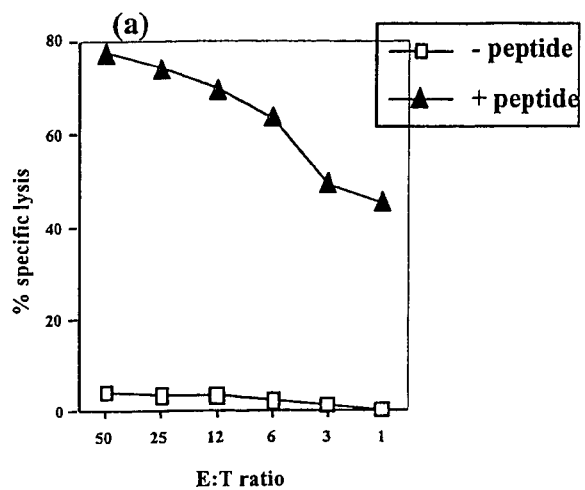
FIGS. 13A-13D are line graphs showing that immunization with LADC elicits functional activation of CD8+ T cells and high levels of cytotoxicity.
Figure 13B:
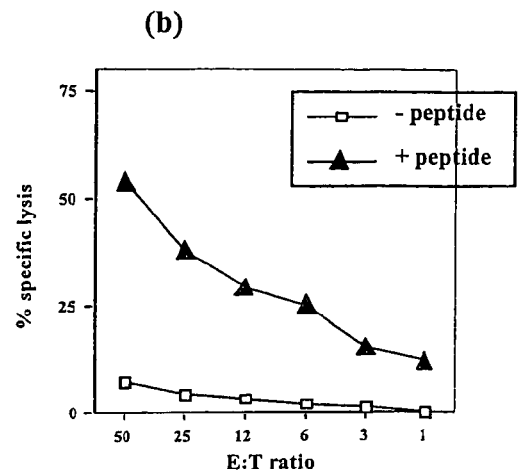
Figure 13C:
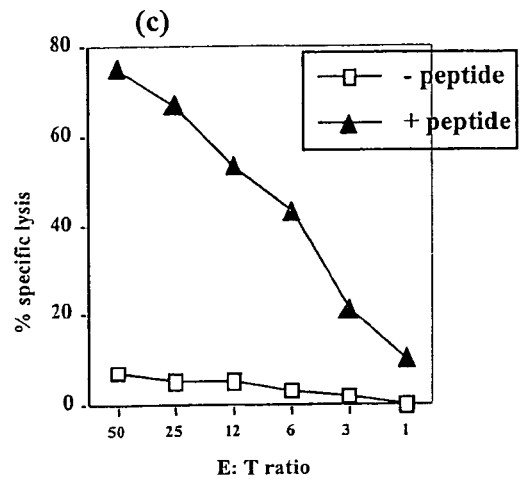
Figure 13D:
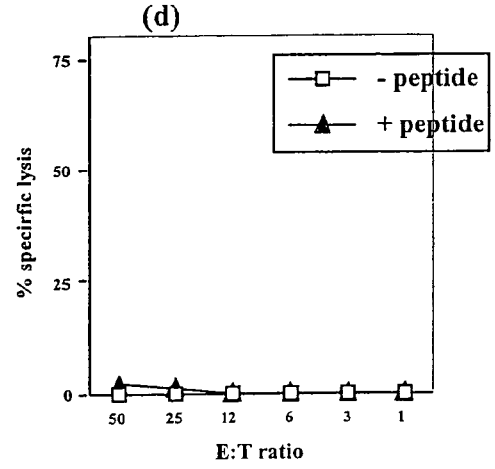

The following example shows that immunization using LADC elicits functional activation of T cells and production of IFN-γ. Generation of functionally active T cells following LADC immunization was assessed using cytokine release assays. Mice were immunized intraperitoneally with either SIINFEKL-LADC (LADC-peptide) or ova-LADC (FIG. 12A), or trp-2 LADC or CLDC alone (LDC) (FIG. 12B). Spleens from immunized mice (4 per group) were then restimulated in vitro for 24 h with the appropriate peptides and the concentration of IFN-γ in the supernatants was assessed by ELISA. Immunization with LADC elicited high levels of the key immunoregulatory cytokine IFN-γ, indicative of functional activation. In contrast, IL-4 was not produced (data not shown). Thus, immunization with LADC generates functionally active T cells of the Th1 phenotype.

Example 13

The following example demonstrates that immunization with LADC elicits functional activation of CD8+ T cells and high levels of cytotoxicity.

The ability of immunization with LADC to elicit functionally active T cells was also assessed using cytotoxicity assays. Spleen cells from mice (3-4 per group) immunized with ova-LADC by the IV route (FIG. 13A) or the SC route (FIG. 13B), or with trp-2-LADC by the IV route (FIG. 13C) or unvaccinated control mice (FIG. 13D) were restimulated with relevant peptides for 5 days in the presence of recombinant human interleukin-2 (rhuIL-2). The effector T cells were then incubated for 4 h with chromium labeled target cells that were either pulsed with relevant SIINFEKL (SEQ ID NO:1) or trp-2 peptides ("peptide+") or were unpulsed controls ("peptide−"). The percentage specific lysis was calculated and plotted for each group. FIGS. 13A-D show that immunization with ova or trp-2 elicited high levels of peptide-specific cytotoxic activity. Thus, LADC immunization elicits high levels of functionally active T cells with strong cytotoxic activity.

Example 14

The following example demonstrates that therapeutic vaccination with LADC controls the growth of established tumors.

Figure 14:
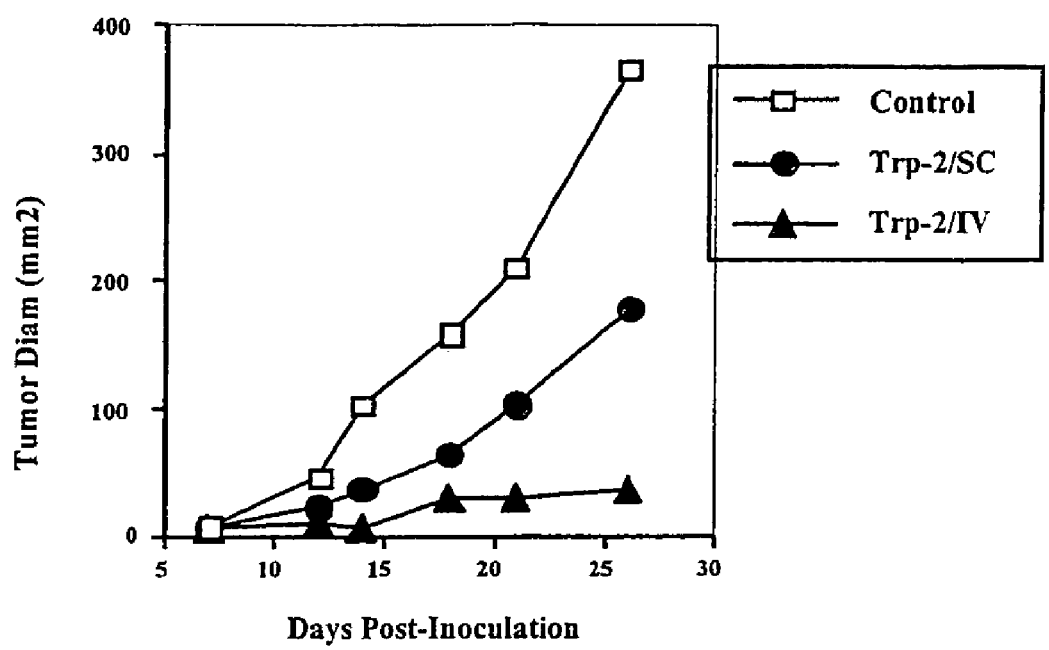
FIG. 14 is a line graph showing that therapeutic vaccination with LADC controls the growth of established tumors.

The ability of LADC immunization to elicit therapeutic anti-tumor immunity was assessed using the B16 tumor model. Mice (5 per group) with day 7 established B16 SC tumors were immunized with LADC prepared with trp-2 peptide (5 µg per mouse) by either the IV or SC routes. Three immunizations were administered at 7 day intervals and the effect on tumor growth was assessed by serial measurements of tumor volume. Untreated mice served as controls. FIG. 14 shows that immunization with trp-2 LADC by either the SC or IV routes significantly inhibited the growth of established B16 tumors. Thus, LADC immunization, using even a weak tumor antigen, elicited sufficient T cell immunity to control the growth of even a very aggressive tumor such as B16.

Example 15

The following example shows that immunization with LADC elicits strong CD4+ T cell responses.

Figure 15:
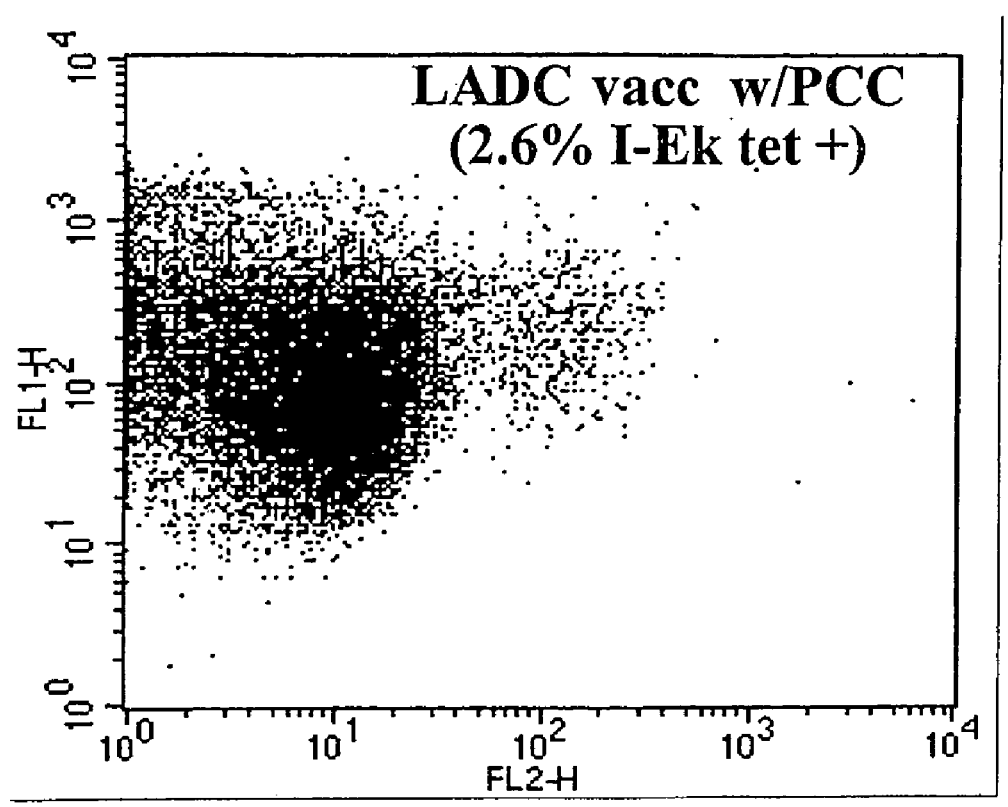
FIG. 15 is a plot showing that immunization with LADC elicits strong CD4+ T cell responses.
Figure 16:
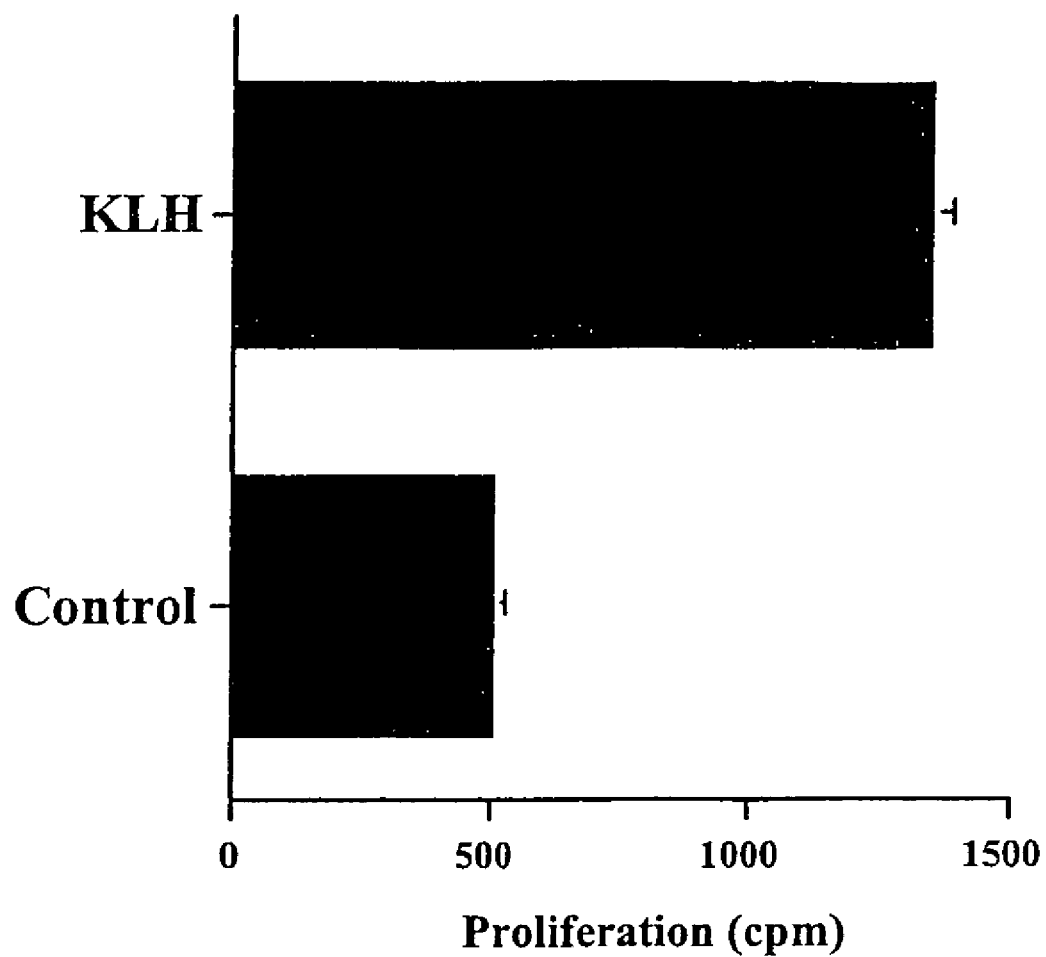
FIG. 16 is a bar graph showing that immunization with LADC elicits CD4+ T cell responses in dogs.
Figure 17:
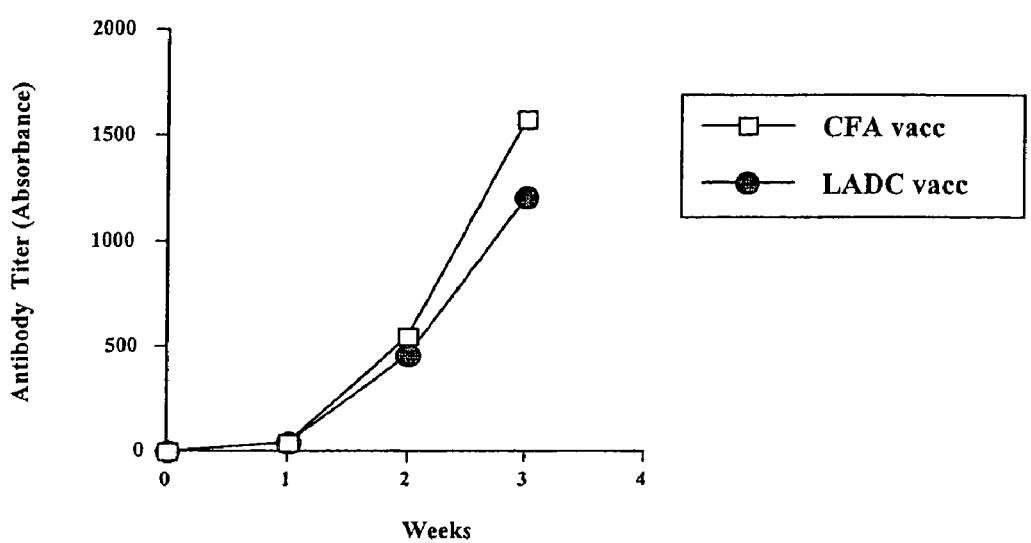
FIG. 17 is a line graph showing that immunization with LADC elicits strong antibody responses.

The inventors assessed the ability of LADC immunization to elicit CD4+ T cell responses by using a peptide (pigeon cytochrome c; PCC) that binds to the class II MHC. CD4+ T cell responses were enumerated using MHC class II tetramers (I-Ek), as described for MHC class I tetramers in Example 6. Mice (3 per group) were immunized with LADC containing either the PCC protein or the PCCV MHC class II-binding peptide. Mice were immunized by the SC or IP routes twice, 7d apart, then spleen cells were collected and immunostained with tetramer and analyzed by flow cytometry. FIG. 15 shows that immunization with either peptide or whole protein elicited a significant increase in numbers of antigen-specific CD4+ T cells. Untreated control mice did not have detectable PCC-specific T cells (data not shown). The IP route of immunization was consistently most effective, consistent with the results observed previously for CD8+ T cell responses. Moreover, the CD4+ T cell response to LADC immunization was also much stronger than the CD4+ T cell response to either peptide and Freund's adjuvant or peptide-pulsed dendritic cells (data not shown). These results indicated that LADC can be used to efficiently elicit both CD8+ and CD4+ T cell responses, thus giving balanced T cell immune responses.

Example 16

The following example shows that immunization with LADC elicits CD4+ T cell responses in dogs.

The inventors assessed the ability of LADC vaccination to elicit CD4+ cell responses in dogs. A dog with osteosarcoma was immunized with an autologous tumor lysate vaccine prepared using LADC. A novel antigen (keyhole limpet hemacyanin; KLH) was also added to the vaccine in order to elicit CD4+ T cell responses. The dog was immunized 3 times with the LADC vaccine, receiving 50 µg KLH with each vaccine. PBMC were collected after the third immunization and incubated for 5 days in 10 µg/ml KLH in quadruplicate wells in vitro and proliferation was assessed using 3H uptake. Unstimulated PBMC served as a control. Significant proliferative responses to KLH were observed, indicative of CD4+ T cell immunity. In addition, the dog mounted a strong DTH response to intradermal skin testing with the KLH antigen (data not shown). These results indicate that LADC can be used to induce CD4+ T cell responses in a large, outbred animal, using even low antigen doses.

Example 17

The following example demonstrates that immunization with LADC elicits strong antibody responses.

The present inventors assessed the ability of LADC to elicit humoral immune responses by immunizing mice with low doses (10 µg per mouse) or ovalbumin protein. In addition, the inventors compared the antibody response to LADC immunization to that elicited by immunization with ova protein in conventional Freund's complete adjuvant (CFA). Mice (4 per group) were immunized once, then boosted 2 weeks later. Serum was collected prior to immunization then at one week intervals after immunization. Antibody titers to ova were quantitated using an ELISA assay. Immunization with LADC was very effective in eliciting antibody responses when compared to a standard method of immunization (antigen in CFA). These data indicate that LADC-based vaccines, in addition to eliciting T cell immunity, are also very effective in eliciting humoral immunity.

Example 18

The following example demonstrates that immunization with LADC elicits virus-specific CD8+ T cells.

Figure 18A:
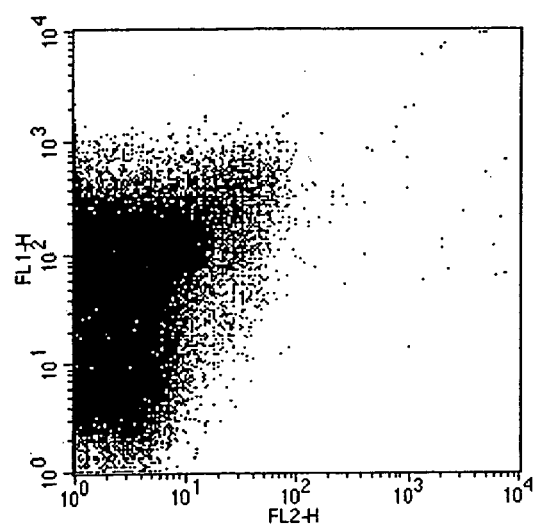
FIGS. 18A-18B are plots showing that immunization with LADC elicits virus-specific CD8+ T cells.
Figure 18B:
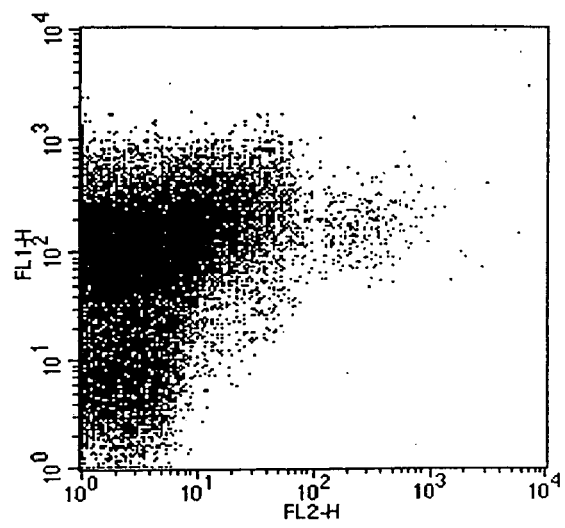

The ability of the LADC vaccine to elicit immunity against viral antigens was assessed using an antigen from the Sendai virus. Mice were immunized twice with 5 µg peptide in the LADC vaccine. Five days after the second vaccination, spleen cells were collected and immunostained with Kb-Sendai peptide tetramers and analyzed by flow cytometry. As shown in FIG. 18, there was a substantial expansion in the number of Sendai specific CD8+ T cells in Sendai vaccinated mice (FIG. 18A), compared to control mice (FIG. 18B). These data illustrate that the LADC vaccine is versatile and can also be used to generate effective antiviral immunity, in addition to antitumor immunity.

Example 19

The following example demonstrates that vaccination against viral antigens using LADC elicits high levels of IFN-γ production by virus antigen-specific T cells.

Figure 19:
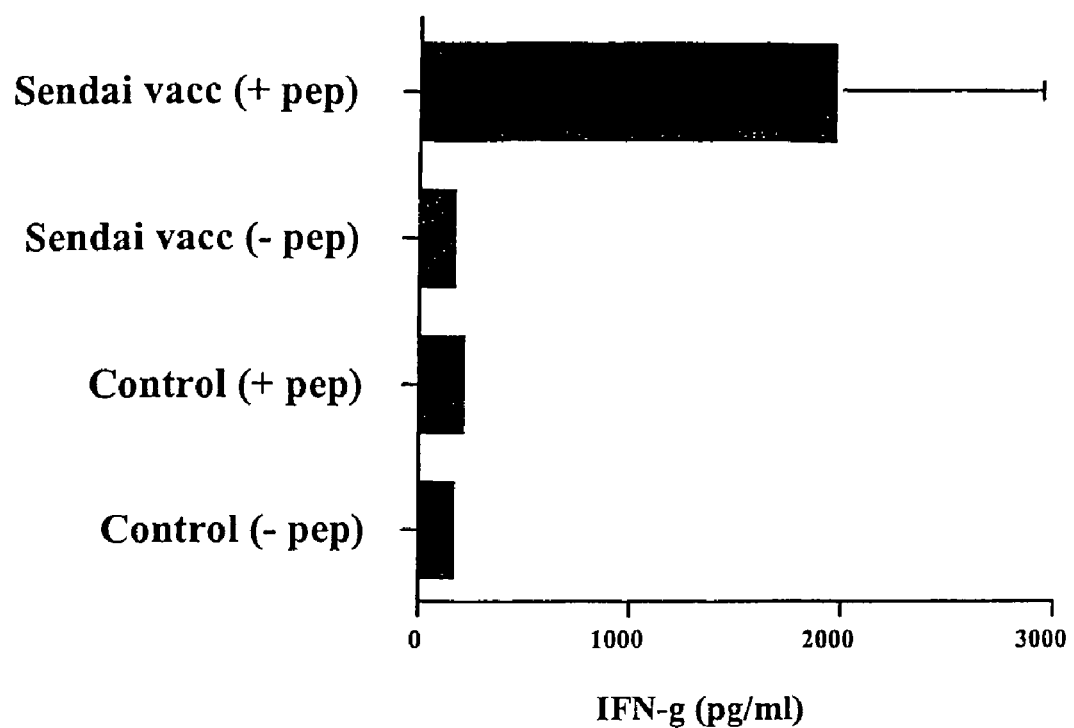
FIG. 19 is a bar graph showing that vaccination against viral antigens using LADC elicits high levels of IFN-γ production by virus antigen-specific T cells.

Mice (3 per group) were immunized twice with LADC containing 5 µg of Sendai virus peptide. Spleen cells were collected and re-stimulated for 18 h in vitro, either with ("+pep") or without ("−pep") Sendai virus peptide. Supernatants from the spleen cultures were then assayed for production of IFN-γ by ELISA. As shown in FIG. 19, immunization with LADC Sendai peptide elicited high levels of virus-antigen specific production of IFN-γ. In contrast, re-stimulation of spleen cells from non-vaccinated (control) mice in vitro with virus peptide did not elicit IFN-γ production. These data indicate that LADC immunization against viral antigens elicits functionally active, antigen-specific T cells.

In summary, the examples presented above show:

1. Vaccination using lipid-DNA complexes and pools of tumor antigens prepared from tumor lysates is an effective means of generating CD8+ T cell responses against established tumors. Induction of antitumor activity has been observed in both experimental rodent models and in dogs with spontaneous tumors.

2. Lipid-DNA complexes combined with defined antigenic peptides can elicit strong antigen-specific CD8+ and CD4+ T cell responses following immunization in vivo, using even very low antigen doses.

3. Vaccines comprised of antigens plus lipid-DNA complexes are more effective in eliciting T cell response that currently available vaccine technologies, including dendritic cell immunization.

4. Lipid-DNA vaccines are sufficiently potent to elicit T cell responses against even weak antigens such as endogenous tumor antigens.

5. Use of lipid-DNA complexes to vaccinate against protein antigens elicits surprisingly potent CD8+ T cell responses. This result is quite unexpected given the inherent difficulties associated with elicitation of CD8+ T cell responses against protein antigens in general.

6. Immunization with lipid-DNA-antigen complexes also generates effective humoral immune responses.

7. Lipid-antigen-DNA complexes can also be used to generate effective T cell immunity against viruses. The immune response elicited includes high levels of virus-specific CD8+ T cells; these virus-specific T cells also produce high levels of IFN-γ.

8. The effectiveness of lipid-DNA-protein/peptide vaccines can be readily translated to large animal spontaneous disease models, including dogs and cats. Thus, the effectiveness of lipid-DNA-antigen vaccines is not restricted to any one species of animal. This result is consistent with the broad cross-species immune activating properties of cationic lipid-DNA complexes in general.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method for eliciting a systemic, non-antigen-specific immune response in a mammal, comprising administering to said mammal an amount of a composition effective to elicit said immune response, wherein said composition comprises:
  a. a cationic liposome delivery vehicle; and
  b. an isolated nucleic acid molecule comprising an isolated bacterially-derived nucleic acid vector without a gene insert or a fragment thereof.

2. The method of claim 1, wherein said liposome delivery vehicle comprises lipids selected from the group consisting of multilamellar vesicle lipids and extruded lipids.

3. The method of claim 1, wherein said liposome delivery vehicle comprises multilamellar vesicle lipids.

4. The method of claim 1, wherein said liposome delivery vehicle comprises pairs of lipids selected from the group consisting of DOTMA and cholesterol; DOTAP and cholesterol; DOTIM and cholesterol, and DDAB and cholesterol.

5. The method of claim 1, wherein said liposome delivery vehicle comprises DOTAP and cholesterol.

6. The method of claim 1, wherein said composition further comprises a pharmaceutically acceptable excipient.

7. The method of claim 6, wherein said excipient comprises a non-ionic diluent.

8. The method of claim 7, wherein said excipient is 5 percent dextrose in water.

9. The method of claim 1, wherein said composition has a nucleic acid to lipid ratio of from about 1:1 to about 1:64.

* * * * *